(12) United States Patent
Kondo et al.

(10) Patent No.: US 11,475,568 B2
(45) Date of Patent: Oct. 18, 2022

(54) METHOD FOR CONTROLLING DISPLAY OF ABNORMALITY IN CHEST X-RAY IMAGE, STORAGE MEDIUM, ABNORMALITY DISPLAY CONTROL APPARATUS, AND SERVER APPARATUS

(71) Applicant: Panasonic Corporation, Osaka (JP)

(72) Inventors: Kenji Kondo, Ibaraki (JP); Jun Ozawa, Nara (JP); Hirohiko Kimura, Fukui (JP); Harumi Itoh, Fukui (JP); Shinichi Fujimoto, Fukui (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 80 days.

(21) Appl. No.: 17/088,663

(22) Filed: Nov. 4, 2020

(65) Prior Publication Data

US 2021/0049766 A1 Feb. 18, 2021

Related U.S. Application Data

(63) Continuation of application No. PCT/JP2019/016947, filed on Apr. 22, 2019.

(30) Foreign Application Priority Data

May 16, 2018 (JP) .............................. JP2018-094738

(51) Int. Cl.
*G06K 9/00* (2022.01)
*G06T 7/00* (2017.01)
(Continued)

(52) U.S. Cl.
CPC ............ *G06T 7/0014* (2013.01); *A61B 6/463* (2013.01); *A61B 6/469* (2013.01); *A61B 6/50* (2013.01);
(Continued)

(58) Field of Classification Search
CPC ....... G06T 7/0014; G06T 3/4046; G06T 7/62; G06T 7/70; G06T 2207/10116;
(Continued)

(56) References Cited

U.S. PATENT DOCUMENTS

2005/0254617 A1* 11/2005 Nishide ................. G06T 11/005
378/4
2006/0280347 A1* 12/2006 Shirahata ............... A61B 6/463
382/128

(Continued)

FOREIGN PATENT DOCUMENTS

JP 2005-323628 11/2005
JP 2018-064627 4/2018
(Continued)

OTHER PUBLICATIONS

International Search Report of PCT application No. PCT/JP2019/016947 dated Jul. 16, 2019.
(Continued)

*Primary Examiner* — Xin Jia
(74) *Attorney, Agent, or Firm* — Wenderoth, Lind & Ponack, L.L.P.

(57) ABSTRACT

A method for controlling display of an abnormality includes obtaining a target chest X-ray image, detecting a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line, calculating an indicator for determining the abnormal state from the structure, comparing the indicator with a reference indicator, and determining whether the structure is in the abnormal state, and displaying, if it is determined that the structure is in the abnormal state, an image of an area of the target chest X-ray image including
(Continued)

the structure determined to be in the abnormal state and details of the abnormal state.

17 Claims, 38 Drawing Sheets

(51) Int. Cl.

| | | |
|---|---|---|
| *G06T 7/62* | (2017.01) | |
| *G06T 7/70* | (2017.01) | |
| *G16H 50/50* | (2018.01) | |
| *G16H 50/20* | (2018.01) | |
| *G16H 30/40* | (2018.01) | |
| *G06N 20/00* | (2019.01) | |
| *A61B 6/00* | (2006.01) | |
| *G06T 3/40* | (2006.01) | |
| *A61B 5/055* | (2006.01) | |
| *A61B 6/03* | (2006.01) | |

(52) U.S. Cl.
CPC ........... *A61B 6/5217* (2013.01); *G06N 20/00* (2019.01); *G06T 3/4046* (2013.01); *G06T 7/62* (2017.01); *G06T 7/70* (2017.01); *G16H 30/40* (2018.01); *G16H 50/20* (2018.01); *G16H 50/50* (2018.01); *A61B 5/055* (2013.01); *A61B 6/032* (2013.01); *G06T 2207/10116* (2013.01); *G06T 2207/20081* (2013.01); *G06T 2207/20084* (2013.01)

(58) Field of Classification Search
CPC . G06T 2207/20081; G06T 2207/20084; G06T 2207/30004; A61B 6/463; A61B 6/469; A61B 6/50; A61B 6/5217; A61B 5/055; A61B 6/032; A61B 6/5205; G06N 20/00; G06N 3/0454; G06N 3/08; G16H 30/40; G16H 50/20; G16H 50/50; G16H 30/20
See application file for complete search history.

(56) References Cited

U.S. PATENT DOCUMENTS

| | | | |
|---|---|---|---|
| 2012/0143090 A1* | 6/2012 | Hay | ......................... A61B 6/505 |
| | | | 600/587 |
| 2018/0108156 A1 | 4/2018 | Kobayashi | |
| 2021/0045704 A1* | 2/2021 | Kondo | ................... G06N 20/00 |

FOREIGN PATENT DOCUMENTS

| | | |
|---|---|---|
| WO | 2005/011501 | 2/2005 |
| WO | 2010/035517 | 4/2010 |
| WO | 2018/069736 | 4/2018 |

OTHER PUBLICATIONS

Xiaosong Wang et al., "ChestX-ray8: Hospital-scale Chest X-ray Database and Benchmarks on Weakly-Supervised Classification and Localization of Common Thorax Diseases", CVPR, May 5, 2017.
Olaf Ronneberger et al., "U-Net: Convolutional Networks for Biomedical Image Segmentation", Medical Image Computing and Computer-Assisted Intervention (MICCAI), Springer, LNCS, vol. 9351, pp. 234-241, Nov. 18, 2015.
Jonathan Long et al., "Fully Convolutional Networks for Semantic Segmentation", In CVPR, Nov. 14, 2014.
Jinwon An et al., "Variational Autoencoder based Anomaly Detection using Reconstruction Probability", SNU Data Mining Center, Feb. 2015 Special Lecture on IE, Dec. 27, 2015.

* cited by examiner

| STEP | STRUCTURE ID (ID = 1, 2, ..., N) | | | |
|---|---|---|---|---|
| | STRUCTURE 1 | STRUCTURE 2 | ... | STRUCTURE N |
| S201 | ✓ | ✓ | | — |
| S202 | STRUCTURE 8 | — | | ✓ |
| S203 | STRUCTURE 4 | — | | — |
| S204 | — | ✓ | | ✓ |
| S205 | — | ✓ | | ✓ |
| S206 | — | STRUCTURE 7 | | STRUCTURE 12 |
| S207 | ✓ | — | | — |

P14a  Q14a

P14b  Q14b

P17a  Q17a

P17b  Q17b

P18a

P19a

P19b

IXj

P20b

Q20c

IXj  P20b  Q20c

IXj

| STRUCTURE ID (ID = 1, 2, ..., N) | RESOLUTION i (i = 0, 1, 2, OR 3) |
|---|---|
| STRUCTURE 1 | 1 |
| STRUCTURE 2 | 2 |
| STRUCTURE 3 | 0 |
| ... | ... |
| STRUCTURE N | 1 |

| STRUCTURE ID (ID=1 TO N) | INDICATOR | ABNORMAL FINDING | DISEASE |
|---|---|---|---|
| STRUCTURE 1 | POSITION | X1 | Y1, Y2 |
| STRUCTURE 1 AND 8 | ANGLE | X2 | Y3 |
| STRUCTURE 1 AND 4 | DISTANCE | X3 | Y4, Y5, Y6 |
| STRUCTURE 1 | NEIGHBORING IMAGE PATTERN | X4 | Y7 |
| STRUCTURE 2 | POSITION | X5 | Y8 |
| STRUCTURE 2 | AREA | X3 | Y9, Y10 |
| ... | ... | ... | ... |

3001  3002  3003  3004

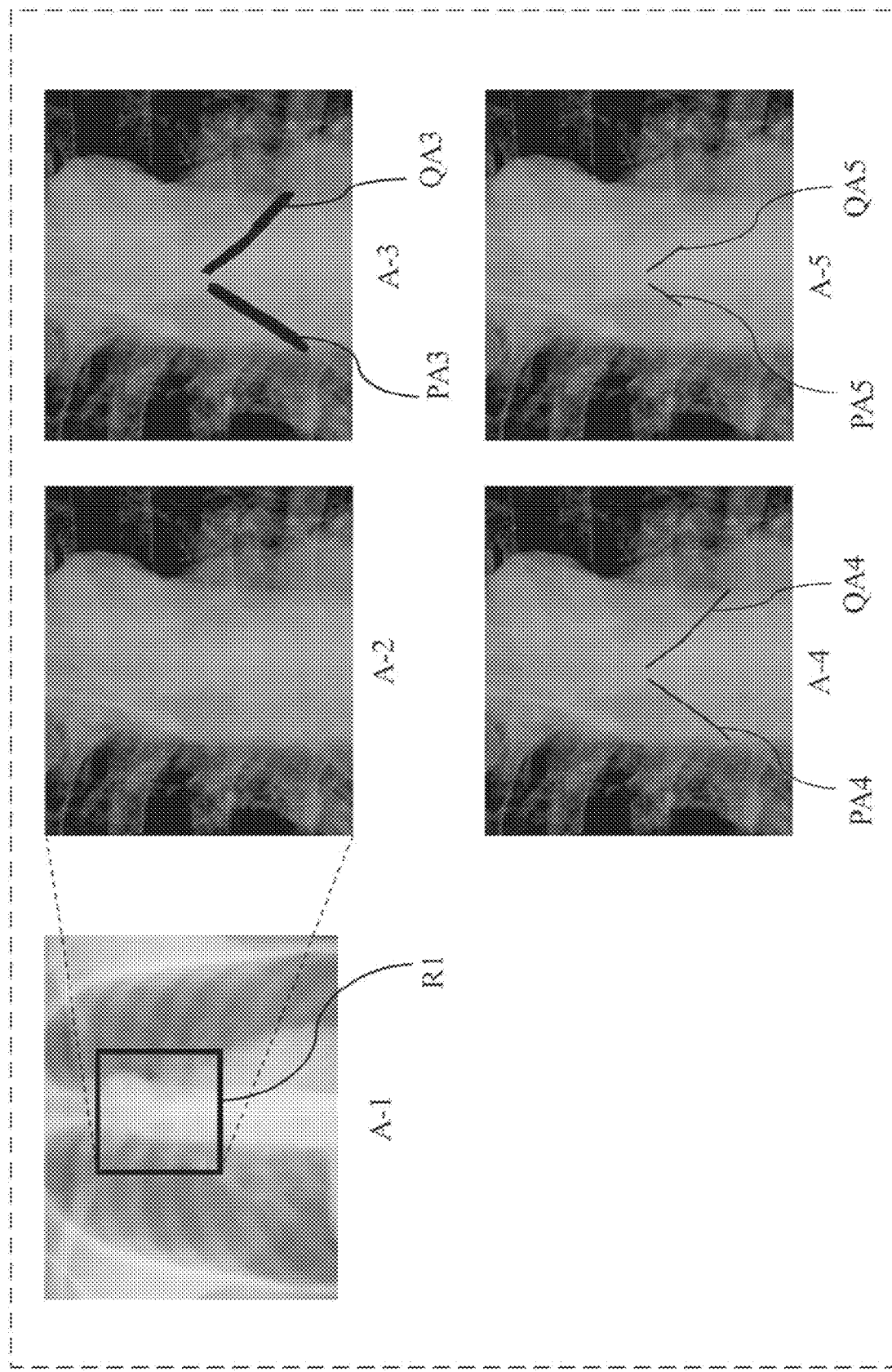

METHOD FOR CONTROLLING DISPLAY OF ABNORMALITY IN CHEST X-RAY IMAGE, STORAGE MEDIUM, ABNORMALITY DISPLAY CONTROL APPARATUS, AND SERVER APPARATUS

BACKGROUND

1. Technical Field

The present disclosure relates to a technique for processing medical images and, more specifically, to a technique for determining an abnormality in a chest X-ray image.

2. Description of the Related Art

During these years, apparatuses, software, and the like that detect lesion areas by analyzing medical images are being developed. A diagnosis that employs such an apparatus, software, or both of them is called "computer-aided detection (CAD)" and expected to reduce a burden on a doctor performing interpretation.

Costs of devices for capturing chest X-ray images and costs of capturing chest X-ray images are especially low among medical images, and such devices are widely used. Chest X-ray images, therefore, are a first choice for making diagnoses of chest diseases.

As disclosed in X. Wang, Y. Peng, L. Lu, Z. Lu, M. Bagheri, and R. Summers, "ChestX-ray8: Hospital-Scale Chest X-Ray Database and Benchmarks on Weakly-Supervised Classification and Localization of Common Thorax Diseases", CVPR, 2017, a method in which machine learning is performed using lesion images of a disease to be detected is one of major CAD techniques for chest X-ray images. In chest X-ray images, however, anatomical structures overlap one another in a depth direction. If such anatomical structures overlap a lesion, therefore, it might be difficult to clearly recognize the lesion. International Publication No. 2010/035517 has proposed a technique to be used in a case where a lesion overlaps anatomical structures and it is difficult to clearly recognize the lesion.

The technique disclosed in International Publication No. 2010/035517 engineeringly achieves doctors' knowledge that a lung field area (i.e., an intercostal area) surrounded by the ribs is focused upon and, if there is a difference in a distance between the left and right ribs, a lesion is suspected. With this technique, an abnormality can be estimated by detecting a change in anatomical structures (i.e., a difference in the distance between the left and right ribs) caused by a lesion, even when it is difficult to clearly recognize the lesion.

SUMMARY

In the above example of the related art, however, further improvements are required in terms of determining various abnormal states with a unified framework independently of certain anatomical structures.

In one general aspect, the techniques disclosed here feature a method for controlling display of an abnormality in a chest X-ray image, the method being performed by a computer of an abnormality display control apparatus that determines an abnormal state from a target chest X-ray image, which is a chest X-ray image to be interpreted, and that displays the abnormal state on a display. The method includes obtaining the target chest X-ray image, detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line, calculating an indicator for determining the abnormal state from the structure, comparing the indicator with a reference indicator obtained in advance, and determining, on a basis of a result of the comparison, whether the structure is in the abnormal state, and displaying, if it is determined that the structure is in the abnormal state, an image of an area of the target chest X-ray image including the structure determined to be in the abnormal state and details of the abnormal state of the structure on the display.

The above aspect achieves further improvements.

It should be noted that this general or specific aspect may be implemented as an apparatus, a system, an integrated circuit, a computer program, a computer-readable storage medium, or any selective combination thereof. The computer-readable storage medium may be a nonvolatile storage medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 9 is a diagram illustrating execution information, in which steps performed for each structure are defined;

FIG. 26 is a diagram schematically illustrating resolution information;

FIG. 30 is a diagram schematically illustrating abnormal finding information;

FIG. 33 is a diagram illustrating a method for calculating a vertex and tangential lines to two linear structures from the linear structures.

DETAILED DESCRIPTION

Figure 1:
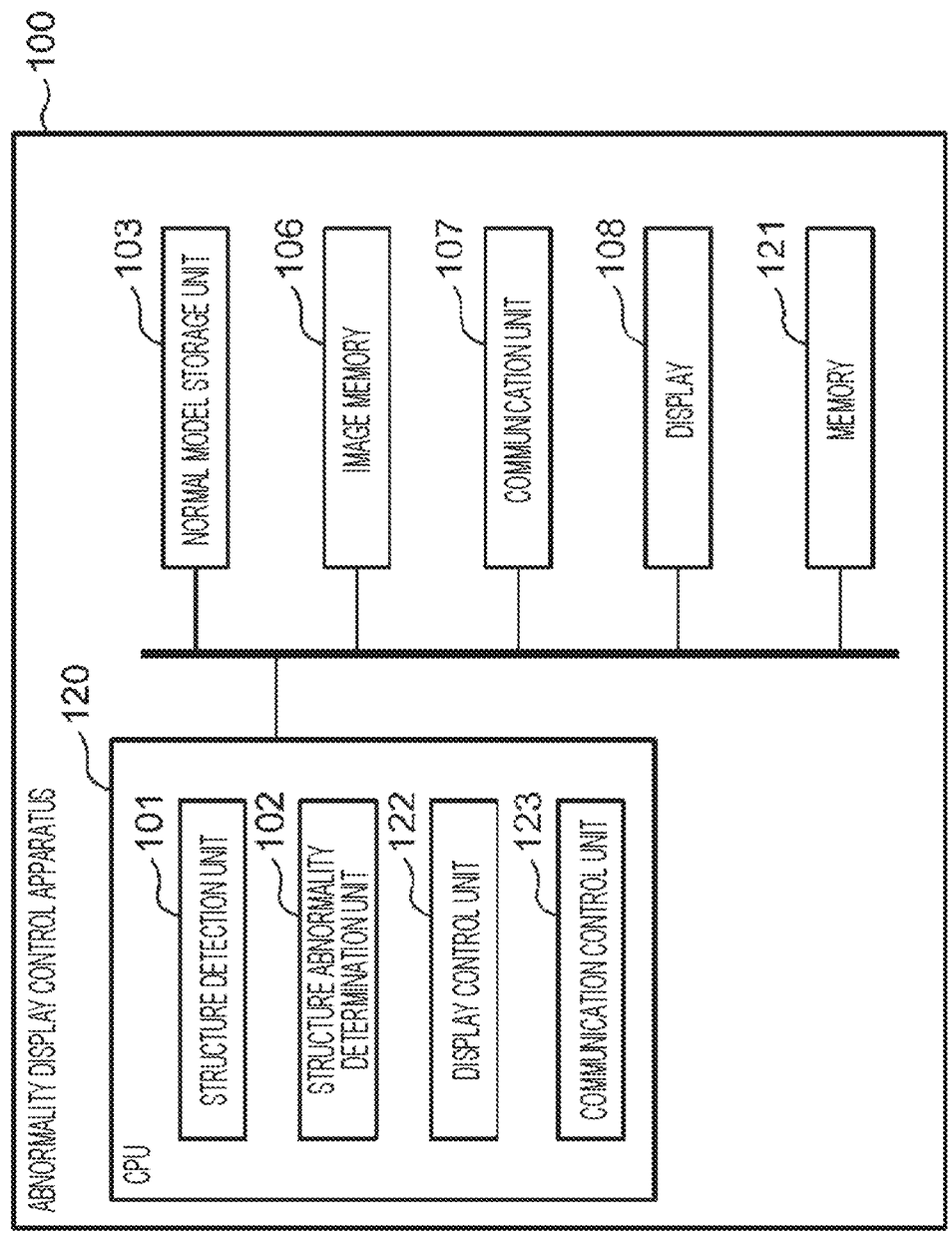
FIG. 1 is a block diagram illustrating an abnormality display control apparatus according to a first embodiment.

Underlying Knowledge Forming Basis of Present Disclosure

As described above, with the method disclosed in X. Wang, Y. Peng, L. Lu, Z. Lu, M. Bagheri, and R. Summers, "ChestX-ray8: Hospital-Scale Chest X-Ray Database and Benchmarks on Weakly-Supervised Classification and Localization of Common Thorax Diseases", CVPR, 2017, it is difficult to detect a lesion that is not clearly recognized. With the method disclosed in International Publication No. 2010/035517, it is difficult to estimate abnormalities other than ones indicated by differences in the area of an intercostal area or differences inthe distance between the left and right ribs. The present inventor, therefore, has focused upon various local structures drawn in chest X-ray images and arrived at the following aspects, in which presence or absence of various abnormalities including ones where it is difficult to clearly recognize a lesion can be determined with a unified framework independently of certain anatomical structures such as the intercostal area.

A first aspect of the present disclosure is a method for controlling display of an abnormality in a chest X-ray image, the method being performed by a computer of an abnormality display control apparatus that determines an abnormal state from a target chest X-ray image, which is a chest X-ray image to be interpreted, and that displays the abnormal state on a display, the method including:

obtaining the target chest X-ray image;

detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;

calculating an indicator for determining the abnormal state from the structure, comparing the indicator with a reference indicator obtained in advance, and determining, on a basis of a result of the comparison, whether the structure is in the abnormal state; and displaying, if it is determined that the structure is in the abnormal state, an image of an area of the target chest X-ray image including the structure determined to be in the abnormal state and details of the abnormal state of the structure on the display.

A second aspect of the present disclosure is a storage medium storing a program for causing a computer of an abnormality display control apparatus that determines an abnormal state from a target chest X-ray image, which is a chest X-ray image to be interpreted, and that displays the abnormal state on a display to perform a process, the storage medium being nonvolatile and computer-readable, the process comprising:

obtaining the target chest X-ray image;

detecting, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;

calculating an indicator for determining the abnormal state from the structure, comparing the indicator with a reference indicator obtained in advance, and determining, on a basis of a result of the comparison, whether the structure is in the abnormal state; and displaying, if it is determined that the structure is in the abnormal state, an image of an area of the target chest X-ray image including the structure determined to be in the abnormal state and details of the abnormal state of the structure on the display.

A third aspect of the present disclosure is an abnormality display control apparatus comprising:

a display;

an obtainer that obtains a target chest X-ray image, which is a chest X-ray image to be interpreted;

a detector that detects, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;

a determiner that calculates an indicator for determining the abnormal state from the structure, that compares the indicator with a reference indicator obtained in advance, and that determines, on a basis of a result of the comparison, whether the structure is in the abnormal state; and a display controller that displays, if it is determined that the structure is in the abnormal state, an image of an area of the target chest X-ray image including the structure determined to be in the abnormal state and details of the abnormal state of the structure on the display.

In the first to third aspects, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line is detected in a target chest X-ray image, which is a chest X-ray image to be interpreted, using a model obtained as a result of machine learning. An indicator for determining an abnormal state is calculated from the structure including the linear structure formed of the first linear area or the second linear area and compared with a predetermined reference indicator, and whether the structure is in the abnormal state is determined on the basis of a result of the comparison. The first and second linear areas are detected regardless of a type of anatomical structure or a position of an anatomical structure in the target chest X-ray image. According to the first to third aspects, therefore, various abnormal states can be determined with a unified framework independently of certain anatomical structures. If it is determined that a structure is in an abnormal state, an image of an area of the target chest X-ray image including the structure determined to be in the abnormal state and details of the abnormal state of the structure are displayed on a display. Beneficial information, therefore, can be presented to a user. As a result, not only an interpretation doctor but also a clinician or a radiologist can give a diagnosis or study by himself/herself, or a medical student can be educated or study by himself/herself.

In the first aspect, for example, the model obtained as a result of the machine learning may be a model subjected to the machine learning such that the structure is detected in a learning chest X-ray image, which is a chest X-ray image in a normal state, using a neural network that performs prediction in units of pixels.

In this aspect, a structure is detected using a model subjected to machine learning such that a structure is detected in a learning chest X-ray image, which is a chest X-ray image in a normal state, using a neural network that performs prediction in units of pixels. Since the prediction is performed in units of pixels, a structure including a linear structure formed of a first linear area or a second linear area can be accurately detected.

In the first aspect, for example, in the detecting, a first X-ray image may be created by converting a resolution of the target chest X-ray image into a first resolution, which is lower than the resolution of the target chest X-ray image, a second X-ray image may be created by converting the resolution of the target chest X-ray image into a second resolution, which is higher than the first resolution but equal to or lower than the resolution of the target chest X-ray image, a structure of a first size may be detected from the first X-ray image, a search area smaller than the second X-ray image may be set in the second X-ray image on a basis of a result of the detection of the structure of the first size, and a structure of a second size, which is smaller than the first size, may be detected in the search area.

In this aspect, a structure of a first size is detected from a first X-ray image of a first resolution. A search area is set in a second X-ray image of a second resolution, which is higher than the first resolution, and a structure of a second size, which is smaller than the first size, is detected in the search area. According to this aspect, therefore, a search area smaller than the target chest X-ray image is set when a high-resolution image is used. As a result, the amount of memory used is reduced. Consequently, even when memory capacity is low, a decrease in structure detection performance can be suppressed.

In the first aspect, for example, in the detection of the structure of the first size, an anatomical structure may be detected from the first X-ray image as the structure of the first size, and in the detection of the structure of the second size, a linear structure may be detected in the search area of the second X-ray image as the structure of the second size.

According to this aspect, since the anatomical structure is of the first size, which is relatively large, the anatomical structure can be appropriately detected from the first X-ray image of the first resolution, which is relatively low. In addition, since the linear structure is of the second size, which is relatively small, the linear structure can be appropriately detected in the search area set in the second X-ray image of the second resolution, which is relatively high.

In the first aspect, for example, in the setting of the search area, the search area may be set using a relative positional relationship between the structure of the first size and the structure of the second size read from a position memory storing the relative positional relationship in advance.

According to this aspect, a position of a structure of the second size can be detected from a position of a structure of the first size obtained as a result of a first detection sub-step and a relative positional relationship between the structure of the first size and the structure of the second size. The structure of the second size, therefore, can be certainly detected by setting a search area such that the search area includes the detected position of the structure of the second size.

In the first aspect, for example, in the determining, a position of the linear structure may be calculated as the indicator.

According to this aspect, when a position of a linear structure is different from one in a normal state, it can be determined that the linear structure is in an abnormal state.

In the first aspect, for example, in the determining, an angle between two linear structures may be calculated as the indicator.

According to this aspect, when an angle between linear structures is different from one in a normal state, it can be determined that one of the linear structures is in an abnormal state.

In the first aspect, for example, in the determining, a distance between the two linear structures may be calculated as the indicator.

According to this aspect, when a distance between two linear structures is different from one in a normal state, it can be determined that one of the linear structures is in an abnormal state.

In the first aspect, for example, in the determining, area of the linear structure may be calculated as the indicator.

According to this aspect, when the area of a linear structure is different from one in a normal state, it can be determined that the linear structure is in an abnormal state.

In the first aspect, for example, in the determining, width of the linear structure may be calculated as the indicator.

According to this aspect, when the width of a linear structure is different from one in a normal state, it can be determined that the linear structure is in an abnormal state.

In the first aspect, for example, in the determining, an image pattern in an area sandwiched by two or more linear structures may be calculated as the indicator.

According to this aspect, when an image pattern in an area sandwiched by two linear structures is not one in a normal state, it can be determined that one of the linear structures is in an abnormal state.

In the first aspect, for example, in the determining, an image pattern in a neighboring area of the linear structure may be calculated as the indicator.

According to this aspect, when an image pattern in an area near a linear structure is different from one in a normal state, it can be determined that the linear structure is in an abnormal state.

In the first aspect, for example, in the determining, whether the structure is in the abnormal state may be determined on a basis of a difference between the reference indicator read from a reference memory storing, as the reference indicator, an indicator calculated from structures detected from chest X-ray images in a normal state and the indicator calculated from the target chest X-ray image.

According to this aspect, an indicator calculated from structures detected from chest X-ray images in a normal state is saved in advance as a reference indicator. Whether a structure is in an abnormal state, therefore, can be accurately determined on the basis of a difference from the reference indicator in a normal state.

The first aspect may further include, for example, reading a correspondence between an abnormal state of one or more structures and an abnormal finding in a chest X-ray image from an abnormal finding memory storing the correspondence and determining an abnormal finding in the target chest X-ray image from the determined abnormal state of the structure using the correspondence; and displaying the determined abnormal finding in the target chest X-ray image on the display.

According to this aspect, an abnormal finding in a target chest X-ray image is determined from a determined abnormal state of each structure using a correspondence saved in an abnormal finding memory in advance. The determined abnormal finding in the target chest X-ray image is displayed on the display. Beneficial information, therefore, can be presented to the user. In addition, since details of the abnormal state of the structure and the abnormal finding in the target chest X-ray image are displayed on the display, the user, such as a clinician, a radiologist, or a medical student, can make a diagnosis, be educated, or study by himself/herself.

A fourth aspect of the present disclosure is a server apparatus including:

an obtainer that obtains a target chest X-ray image, which is a chest X-ray image to be interpreted;

a detector that detects, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;

a determiner that calculates an indicator for determining the abnormal state from the structure, that compares the indicator with a reference indicator obtained in advance, and that determines, on a basis of a result of the comparison, whether the structure is in the abnormal state; and a communication controller that transmits, if it is determined that the structure is in the abnormal state, an image of an area of the target chest X-ray image including the structure determined to be in the abnormal state and details of the abnormal state of the structure to an external terminal apparatus.

In the fourth aspect, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line is detected in a target chest X-ray image, which is a chest X-ray image to be interpreted, using a model obtained as a result of machine learning. An indicator for determining an abnormal state is calculated from the structure including the linear structure formed of the first linear area or the second linear area and compared with a predetermined reference indicator, and whether the structure is in the abnormal state is determined on the basis of a result of the comparison. The first and second linear areas are detected regardless of a type of anatomical structure or a position of an anatomical structure in the target chest X-ray image. According to the fourth aspect, therefore, various abnormal states can be determined with a unified framework independently of certain anatomical structures. If it is determined that a structure is in an abnormal state, an image of an area of the target chest X-ray image including the structure determined to be in the abnormal state and details of the abnormal state of the structure are transmitted to an external terminal apparatus. Beneficial information, therefore, can be presented to a user. As a result, not only an interpretation doctor but also a clinician or a radiologist can give a diagnosis or study by himself/herself, or a medical student can be educated or study by himself/herself.

EMBODIMENTS

Embodiments of the present disclosure will be described hereinafter with reference to the drawings. In the drawings, the same components are given the same reference numerals, and redundant description thereof is omitted as necessary.

First Embodiment

Figure 2:
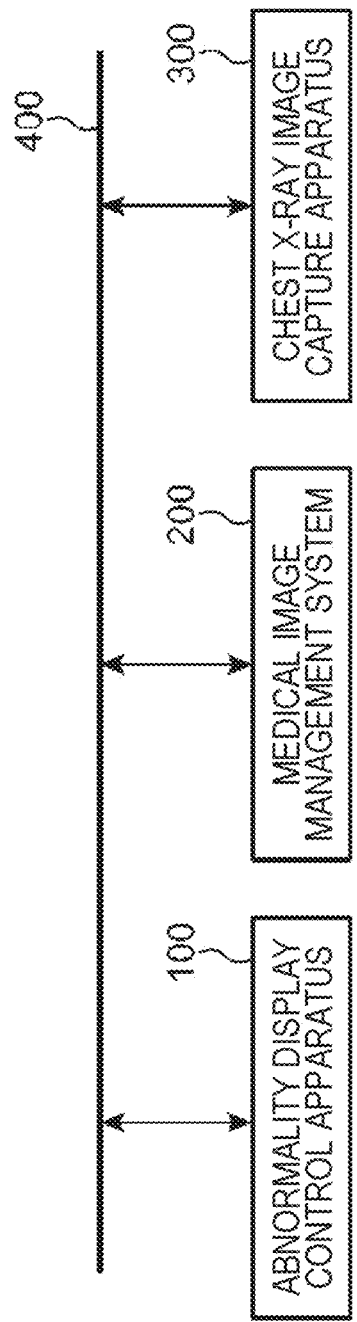
FIG. 2 is a block diagram illustrating a network configuration in a medical facility according to the first embodiment.

FIG. 1 is a block diagram schematically illustrating the configuration of an abnormality display control apparatus 100 that performs a method for controlling display of an abnormality in a chest X-ray image according to a first embodiment. FIG. 2 is a block diagram schematically illustrating a network configuration 410 in a medical facility.

As illustrated in FIG. 2, the network configuration 410 in the medical facility includes an intra network 400. The abnormality display control apparatus 100, a medical image management system 200, and a chest X-ray image capture apparatus 300 are connected to the intra network 400. The medical image management system 200 saves and manages chest X-ray images, computer tomography (CT) images, magnetic resonance imaging (MRI) images, and the like. The chest X-ray image obtaining apparatus 300 captures chest X-ray images of patients and persons who receive a medical examination. Chest X-ray images captured by the chest X-ray image capture apparatus 300 are transmitted and saved to the medical image management system 200.

The abnormality display control apparatus 100, the medical image management system 200, and the chest X-ray image capture apparatus 300 need not necessarily be connected to the intra network 400 in the same medical facility. The abnormality display control apparatus 100 and the medical image management system 200 may be software operating on a server in a data center outside the medical facility, a private cloud server, a public cloud server, or the like. The chest X-ray image capture apparatus 300 may be installed in a hospital or a vehicle that goes around to be used for a medical examination or the like. As the medical image management system 200, a picture archiving and communication system (PACS), for example, is used.

As illustrated in FIG. 1, the abnormality display control apparatus 100 includes a normal model storage unit 103, an image memory 106, a communication unit 107, a display 108, a central processing unit (CPU) 120, and a memory 121. The abnormality display control apparatus 100 is achieved, for example, by a personal computer.

The communication unit 107 communicates with the medical image management system 200 and the like over the intra network 400. The normal model storage unit 103 is achieved, for example, by a hard disk or a semiconductor memory. The normal model storage unit 103 (an example of a reference memory) stores normal states of predefined structures (described later) as a model. The image memory 106 is achieved, for example, by a hard disk or a semiconductor memory. The image memory 106 stores obtained target chest X-ray images. The display 108 is achieved by a liquid crystal monitor, for example, and displays a target chest X-ray image for a doctor or a radiologist, who is a user, to give an image diagnosis or perform image checking after the image is captured. The display 108 also displays chart information regarding a patient for whom the target chest X-ray image has been captured, a report input screen, on which a result of the image diagnosis is entered, and the like.

The memory 121 is achieved, for example, by a semiconductor memory. The memory 121 includes, for example, a read-only memory (ROM), a random-access memory (RAM), and an electrically erasable programmable read-only memory (EEPROM). The ROM of the memory 121 stores a control program for operating the CPU 120 according to the first embodiment.

The CPU 120 executes the control program according to the first embodiment stored in the memory 121 to function as a structure detection unit 101, a structure abnormality determination unit 102, a display control unit 122, and a communication control unit 123. The structure detection unit 101 (an example of a detection unit) detects predefined structures from a target chest X-ray image saved in the image memory 106. The structure abnormality determination unit 102 (an example of a determination unit) refers to a normal model stored in the normal model storage unit 103 and determines whether each of the structures detected by the structure detection unit 101 is in an abnormal state. Functions of the display control unit 122 and the communication control unit 123 will be described later.

Figure 3:
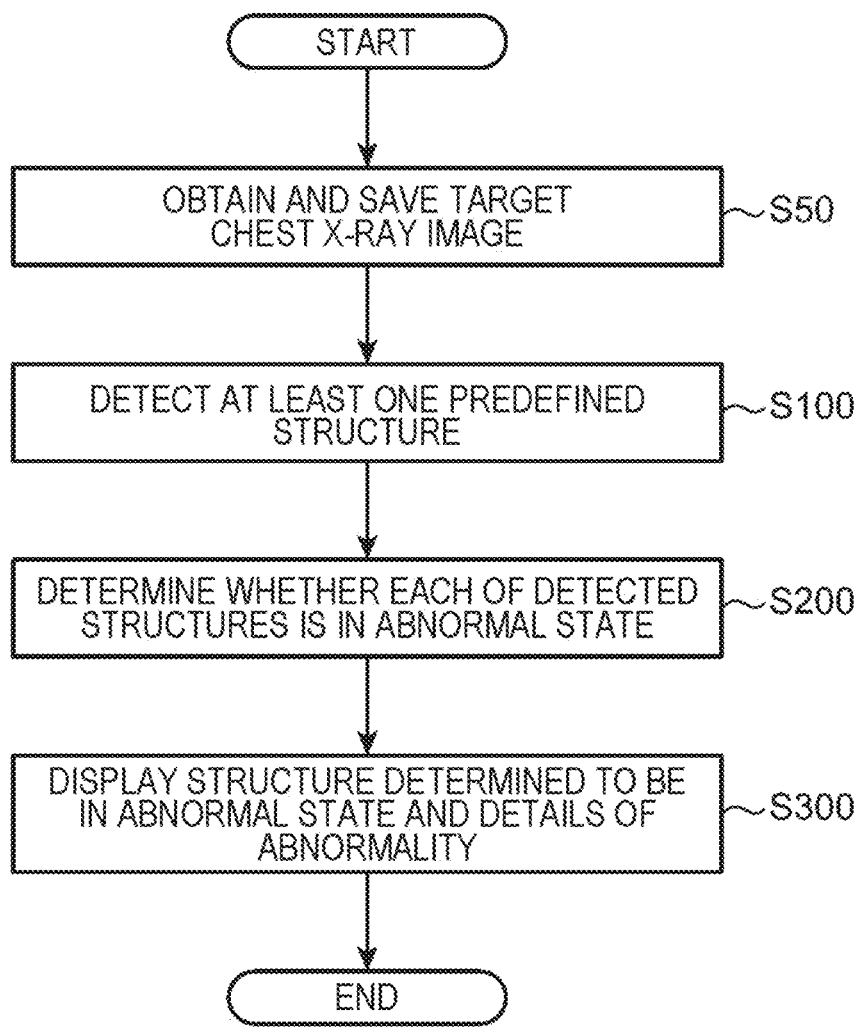
FIG. 3 is a flowchart according to the first embodiment.

FIG. 3 is a flowchart schematically illustrating a process performed by the abnormality display control apparatus 100 according to the first embodiment. First, in step S50, the communication control unit 123 (an example of an obtaining unit) obtains a target chest X-ray image, which is a chest X-ray image to be interpreted, from the medical image management system 200 through the communication unit 107 and saves the obtained target chest X-ray image to the image memory 106. In step S100, the structure detection unit 101 reads the target chest X-ray image from the image memory 106 and detects one or more predefined structures from the target chest X-ray image.

Each of the one or more structures is (i) a line or an area in the chest X-ray image indicating an anatomical structure of a human body, (ii) a line or an area in the chest X-ray image indicating an part of an anatomical structure, or (iii) a boundary line in the chest X-ray image indicating a boundary between anatomical structures whose X-ray transmittances are different from each other.

Each of the one or more structures is classified into a linear structure or an area structure. A linear structure may be a boundary line in a chest X-ray image, a line in a chest X-ray image indicating an anatomical structure, or a line in a chest X-ray image indicating a part of an anatomical structure.

Figure 5A:
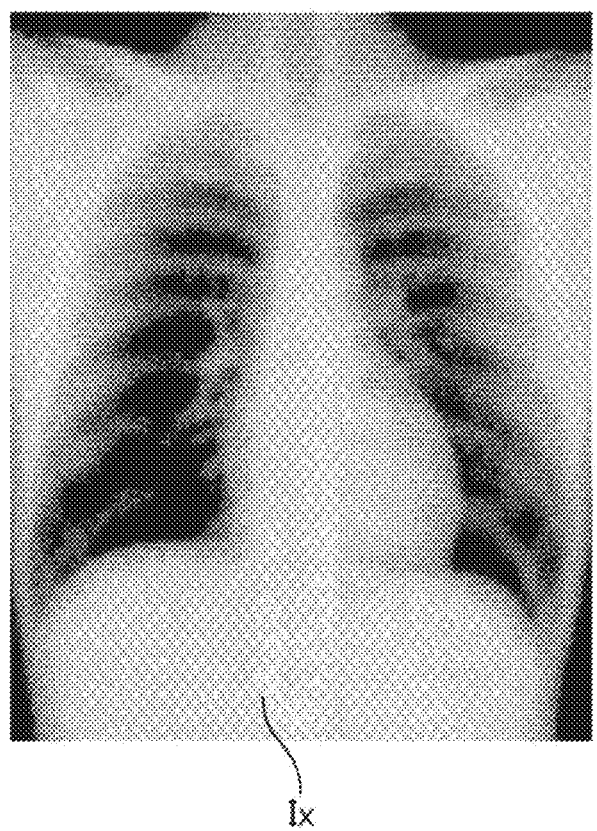
FIG. 5A is a diagram illustrating a chest X-ray image including a shadow in the right dorsal diaphragm.
Figure 5B:
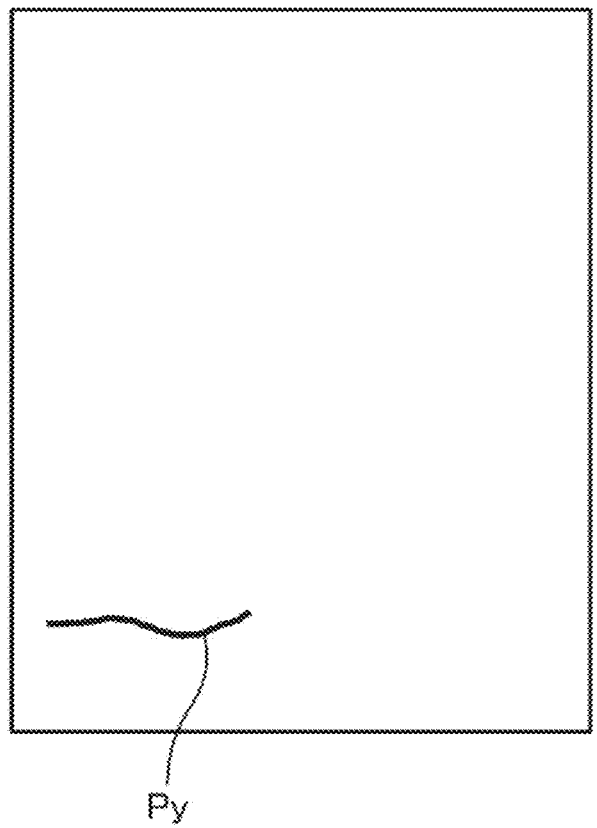
FIG. 5B is a diagram illustrating a mask image of a shadow in the right dorsal diaphragm.
Figure 5C:
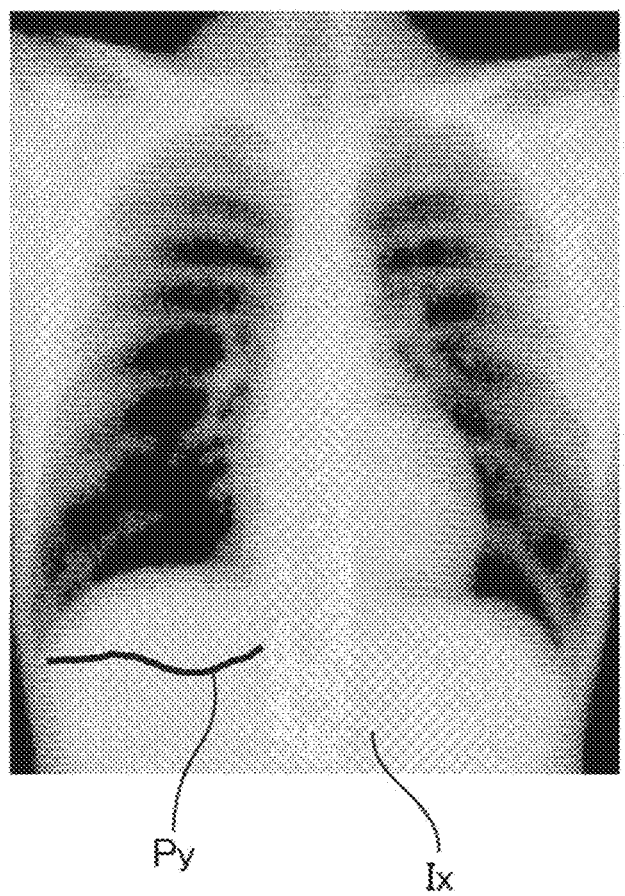
FIG. 5C is a diagram illustrating an image obtained by superimposing the mask image upon the chest X-ray image.
Figure 6A:
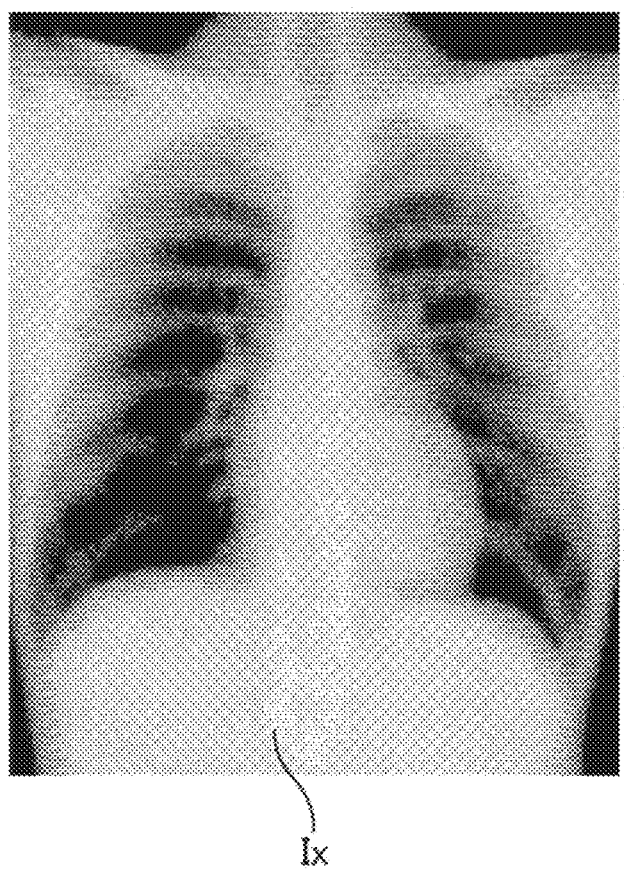
FIG. 6A is a diagram illustrating a chest X-ray image including the first thoracic vertebra.
Figure 6B:
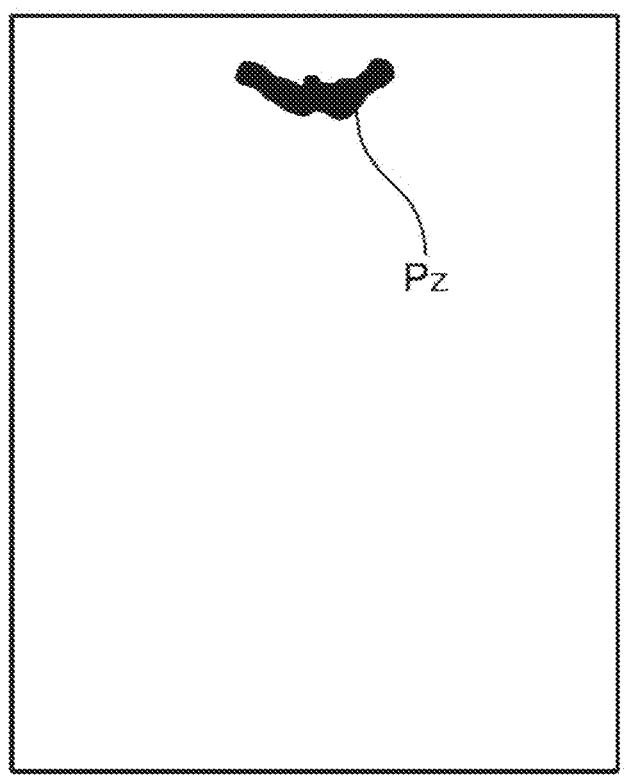
FIG. 6B is a diagram illustrating a mask image of the first thoracic vertebra.
Figure 6C:
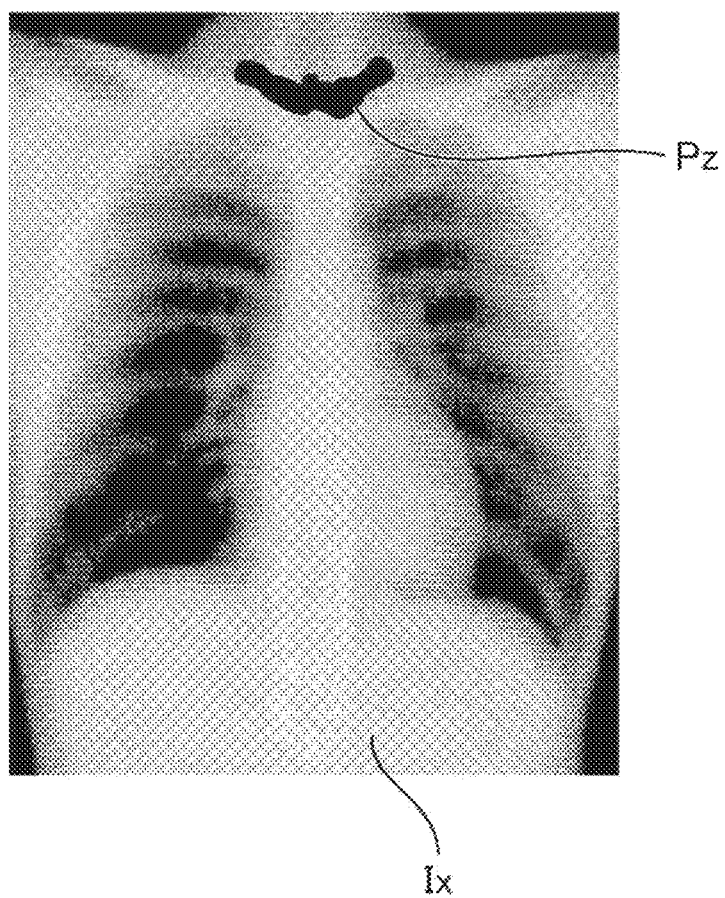
FIG. 6C is a diagram illustrating an image obtained by superimposing the mask image upon the chest X-ray image.

A structure that is not a linear structure, that is, a structure that is not regarded as a line, is defined as an area structure. Because there are linear structures wider than one pixel in images, however, linear structures and area structures can be indistinguishable from each other. For this reason, structures whose length divided by width is equal to or larger than a threshold, for example, may be defined as a linear structure. The threshold may be set at a value with which a structure can be regarded as a line and may be, say, 10, 100, or 1,000. FIGS. 4A to 4C and FIGS. 5A to 5C illustrate examples of the linear structure, and FIGS. 6A to 6C illustrate an example of the area structure.

Figure 4A:
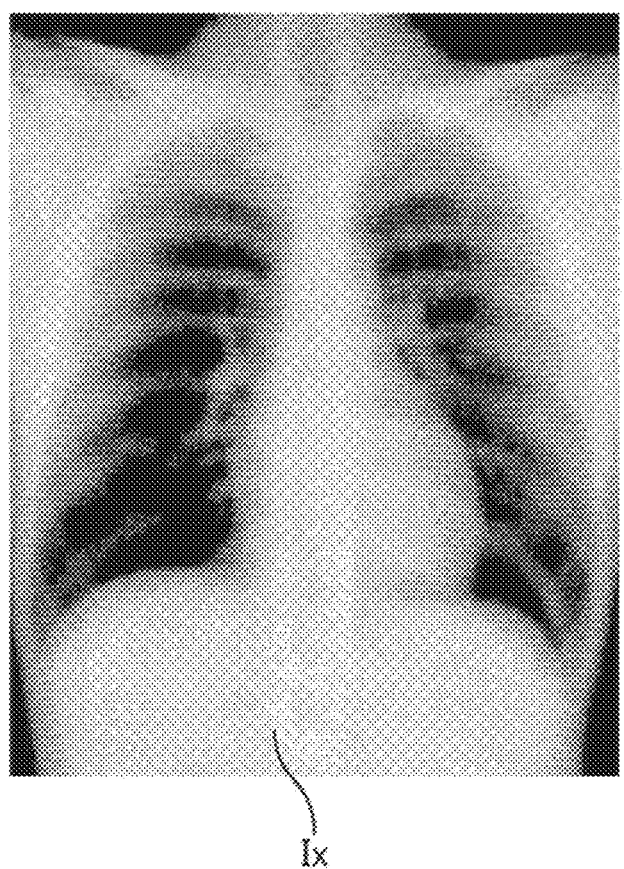
FIG. 4A is a diagram illustrating a chest X-ray image including a shadow in the descending aorta.
Figure 4B:
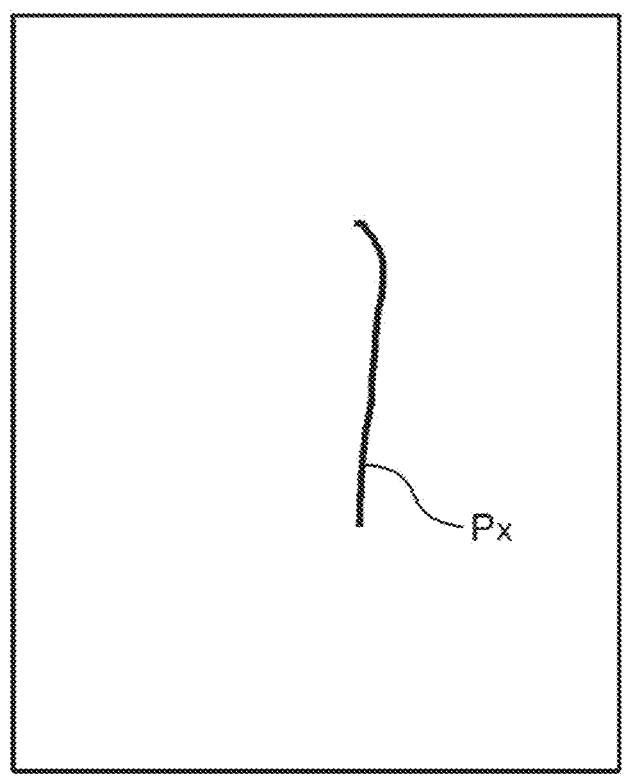
FIG. 4B is a diagram illustrating a mask image of the shadow in the descending aorta.
Figure 4C:
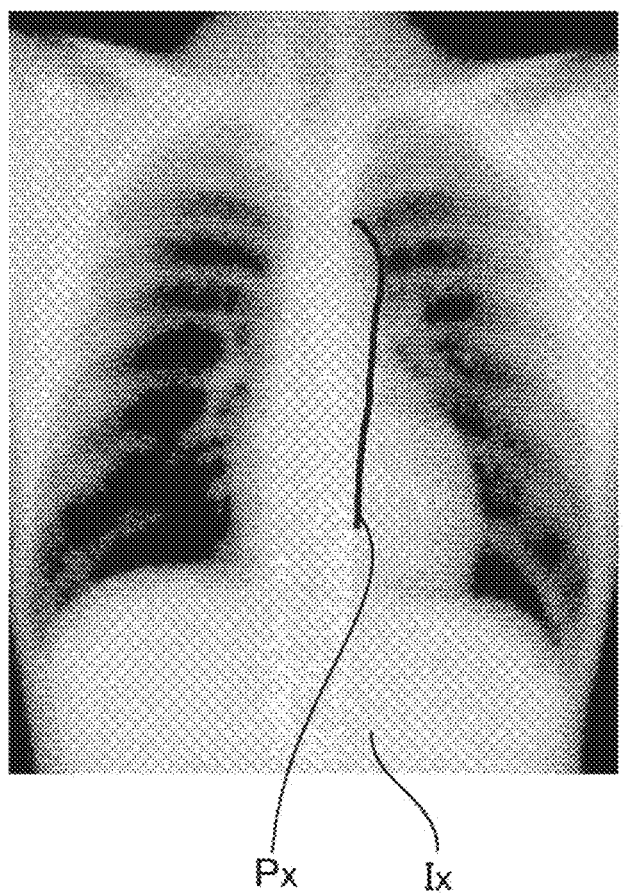
FIG. 4C is a diagram illustrating an image obtained by superimposing the mask image upon the chest X-ray image.

FIG. 4A is a diagram illustrating a chest X-ray image Ix including a shadow in the descending aorta (i.e., a boundary line caused by a difference in X-ray transmittance between the descending aorta and the lung parenchyma; an example of a first linear area). FIG. 4B is a diagram illustrating a mask image Px of the shadow in the descending aorta. FIG. 4C is a diagram illustrating an image displayed by superimposing the mask image Px illustrated in FIG. 4B upon the chest X-ray image Ix illustrated in FIG. 4A. FIG. 5A is a diagram illustrating the chest X-ray image Ix including a shadow in the right dorsal diaphragm (right dorsal lung base) (i.e., a boundary line caused by a difference in X-ray transmittance between a dorsal bottom of the lung parenchyma and ventral organs; an example of the first linear area). FIG. 5B is a diagram illustrating a mask image Py of the shadow in the right dorsal diaphragm. FIG. 5C is a diagram illustrating an image displayed by superimposing the mask image Py illustrated in FIG. 5B upon the chest X-ray image Ix illustrated in FIG. 5A. FIG. 6A is a diagram illustrating a chest X-ray image Ix including an area in which the first thoracic vertebra is projected. FIG. 6B is a diagram illustrating a mask image Pz of the first thoracic vertebra. FIG. 6C is a diagram illustrating an image displayed by superimposing the mask image Pz illustrated in FIG. 6B upon the chest X-ray image Ix illustrated in FIG. 6A.

A mask image expresses an area of a corresponding chest X-ray image occupied by a structure in binary representation or grayscale. In the present embodiment, a binary mask image is employed. A mask image is created and prepared by a person with a medical background as learning data used when the structure detection unit 101 is subjected to machine learning. The structure detection unit 101 subjected to machine learning outputs a mask image as a result of processing of a target chest X-ray image.

In the present embodiment, an artificial neural network is used as means for performing machine learning on the structure detection unit 101. More specifically, U-Net disclosed in O. Ronneberger, P. Fischer, and T. Brox, "U-Net: Convolutional Networks for Biomedical Image Segmentation", Medical Image Computing and Computer-Assisted Intervention (MICCAI), Springer, LNCS, Vol. 9351: 234-241, 2015 is used as an artificial neural network that performs semantic segmentation for extracting a target area from a target image in units of pixels. "Semantic segmentation" refers to area division of an image in units of pixels.

Figure 7:
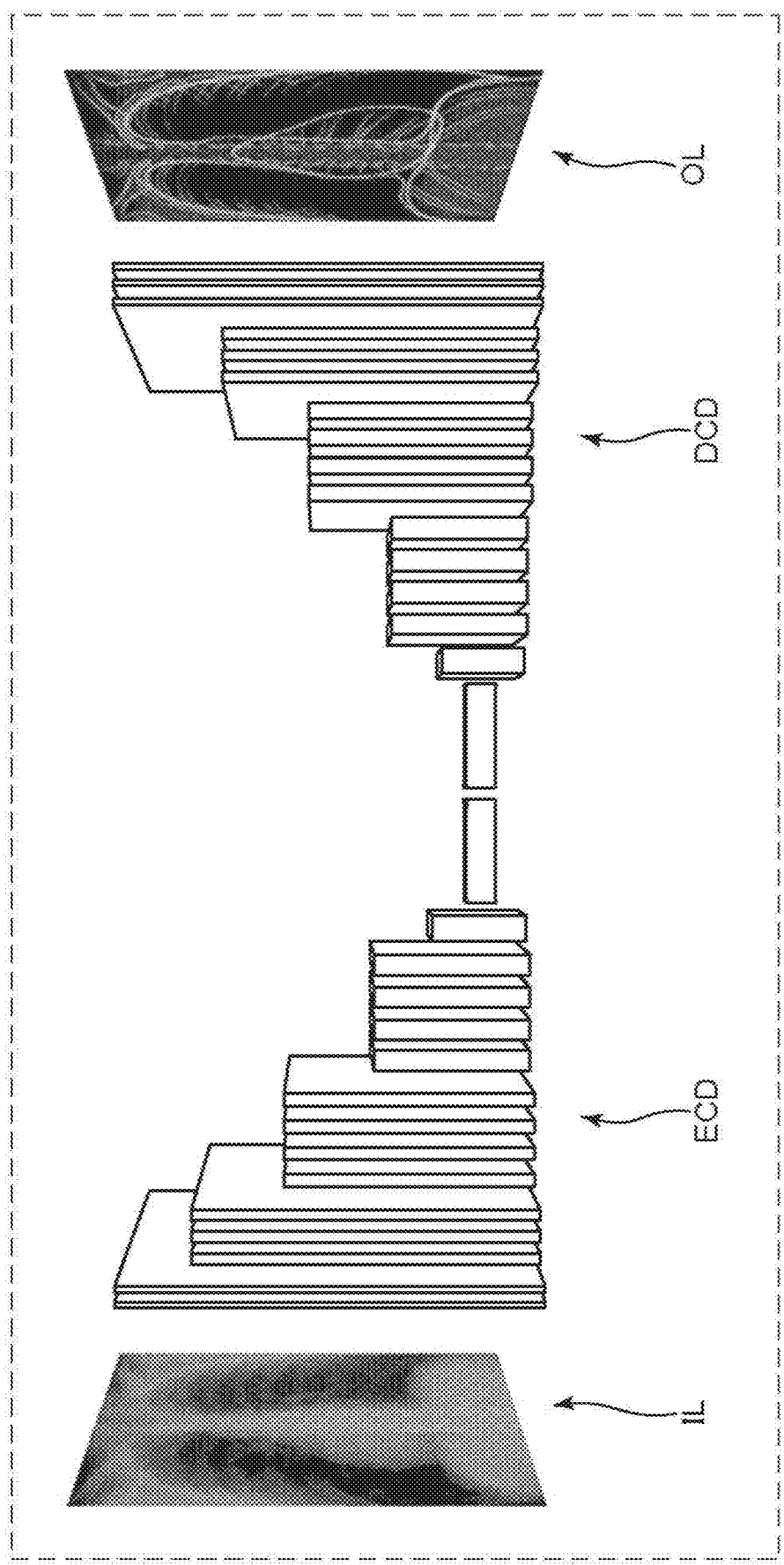
FIG. 7 is a diagram schematically illustrating the architecture of U-Net.

FIG. 7 is a diagram schematically illustrating the architecture of U-Net. U-Net is a convolutional neural network including an encoder ECD and a decoder DCD illustrated in FIG. 7. An input image is input to an input layer IL of U-Net, and U-Net outputs an output image to an output layer OL. Machine learning is performed by giving U-Net a large number of pairs of an input image, such as those illustrated in FIGS. 4A, 5A, and 6A, and a mask image, such as those illustrated in FIGS. 4B, 5B, and 6B.

More specifically, a large number of chest X-ray images Ix, such as that illustrated in FIG. 4A, are input to U-Net, and machine learning is performed such that U-Net outputs mask images Px, such as that illustrated in FIG. 4B. As a result, a structure detection unit 101 for detecting a shadow in the descending aorta is generated. In addition, a large number of chest X-ray images Ix, such as that illustrated in FIG. 5A, are input to U-Net, and machine learning is performed such that U-Net outputs mask images Py, such as that illustrated in FIG. 5B. As a result, a structure detection unit 101 for detecting a shadow in the right dorsal diaphragm is generated. In addition, a large number of chest X-ray images Ix, such as that illustrated in FIG. 6A, are input to U-Net, and machine learning is performed such that U-Net outputs mask images Pz, such as that illustrated in FIG. 6B. As a result, a structure detection unit 101 for detecting the first thoracic vertebra is generated. When a target chest X-ray image is input to the structure detection unit 101 for detecting a shadow in the descending aorta after the machine learning, for example, a shadow in the descending aorta is detected as an area of a structure defined in the machine learning.

In the present embodiment, machine learning is performed on U-Nets that detect a total of N predefined structures (N is an integer equal to or larger than 1) to prepare N U-Nets subjected to the machine learning. These N U-Nets subjected to the machine learning are used as the structure detection unit 101. Alternatively, another neural network, such as one disclosed in L. Long, E. Shelhamer, and T. Darrell, "Fully Convolutional Networks for Semantic Segmentation", CVPR, 2015, may be used instead of U-Net as an artificial neural network that performs semantic segmentation.

In step S200 illustrated in FIG. 3, the structure abnormality determination unit 102 determines whether each of the detected structures is in an abnormal state.

Figure 8A:
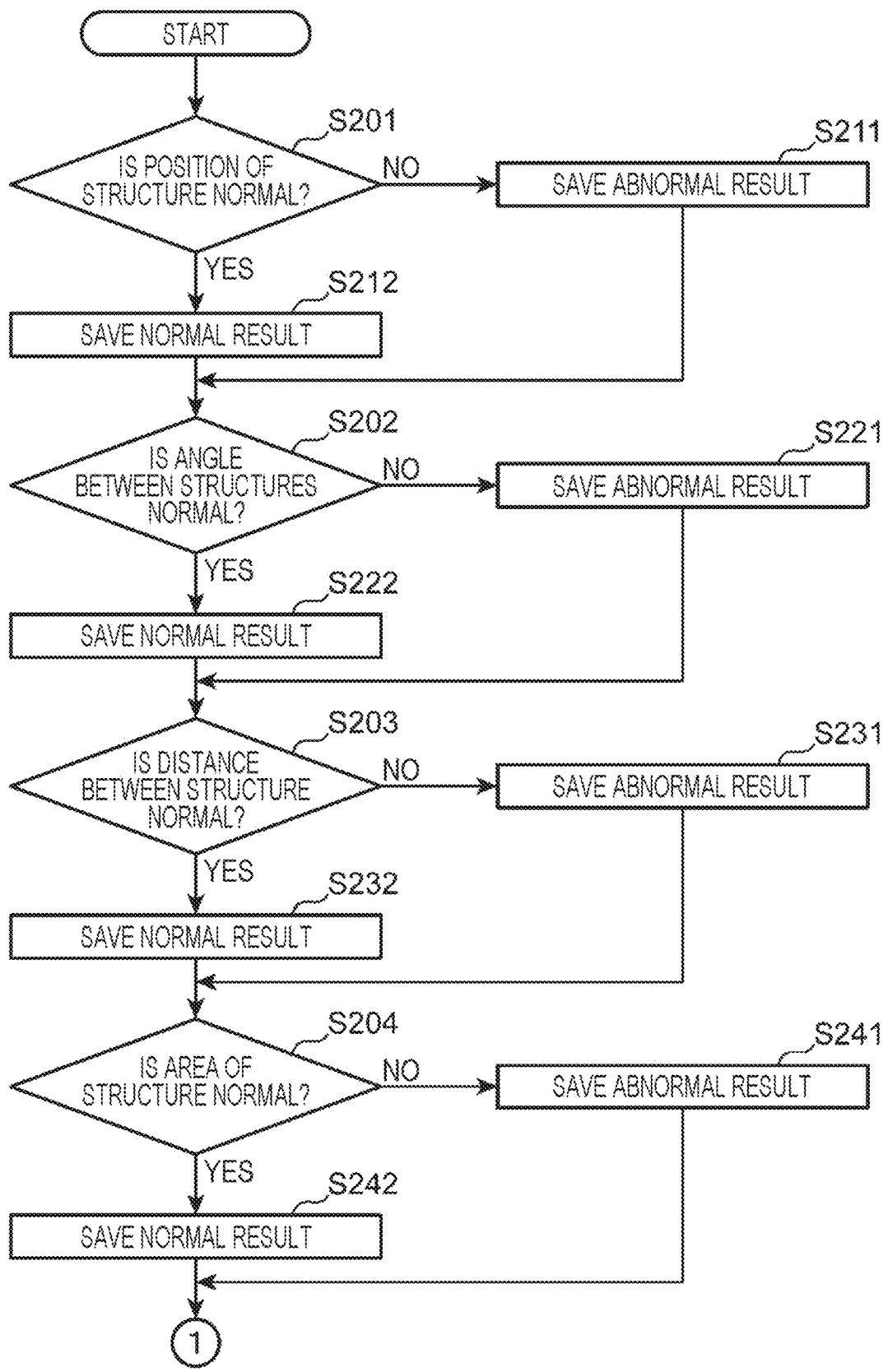
FIG. 8A is a flowchart illustrating a process for determining an abnormality according to the first embodiment.
Figure 8B:
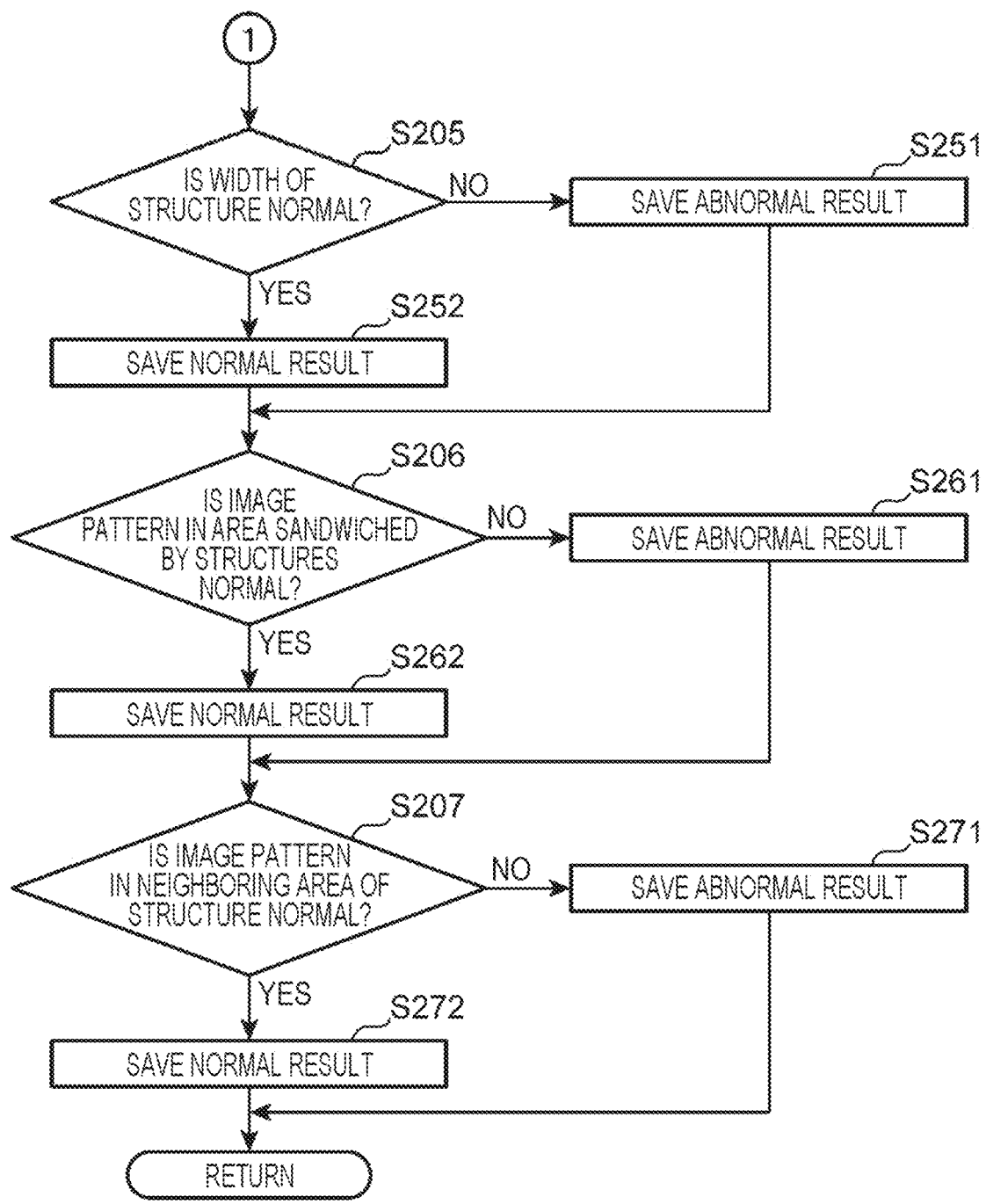
FIG. 8B is a flowchart illustrating the process for determining an abnormality according to the first embodiment.

FIGS. 8A and 8B are flowcharts schematically illustrating a process for determining an abnormality performed in step S200 (FIG. 3). FIG. 9 is a diagram schematically illustrating execution information 900, in which steps illustrated in FIGS. 8A and 8B performed for each structure are defined. As illustrated in FIG. 9, the execution information 900 includes a step field 901 set along a vertical axis and a structure identifier (ID) field 902 set along a horizontal axis.

As illustrated in FIGS. 8A and 8B, the structure abnormality determination unit 102 performs, for each of the detected structures, a determination process based on a position of the structure (step S201), a determination process based on an angle between the structure and another structure (step S202), a determination process based on a distance between structures (step S203), a determination process based on the area of the structure (step S204), a determination process based on the thickness of the structure (step S205), a determination process based on an image pattern in an area sandwiched by the structure and another structure (step S206), and a determination process based on an image pattern in a neighboring area of the structure (step S207). These determination processes will be described in detail later.

In each determination process, an indicator for determining whether a structure is normal or abnormal differs depending on the structure. The execution information 900 illustrated in FIG. 9, which is based on medical knowledge, therefore, is prepared in advance and saved in the memory 121. This is because how an abnormality exhibits differs depending on the structure. The structure abnormality determination unit 102 obtains, from the execution information 900 for each of the detected structures, information indicating whether to perform each of the steps illustrated in the flowcharts of FIGS. 8A and 8B and, when some of the steps are to be performed in relation to another structure, information indicating the other structure.

When a check or a structure ID is shown in a structure ID field 902 of the execution information 900 illustrated in FIG. 9, a corresponding step is to be performed for a corresponding structure. For example, steps S201 to S203 and S207 are performed but steps S204 to S206 are not performed for structure 1. That is, whether structure 1 is in an abnormal state is determined on the basis of a position of structure 1, an angle between structures 1 and 8, a distance between structures 1 and 4, and an image pattern in a neighboring area of structure 1. For example, steps S202 and S204 to S206 are performed but steps S201, S203, and S207 are not performed for structure N. That is, whether structure N is in an abnormal state is determined on the basis of an angle of structure N, the area of structure N, the width of structure N, and an image pattern in an area sandwiched by structures N and 12.

In a method for determining whether a structure is normal or abnormal used in common between steps S201 to S207 in the present embodiment, a normal model is constructed in advance using a large amount of normal data and a structure detected from a target chest X-ray image is compared with the normal model. The normal model constructed in advance is stored in the normal model storage unit 103.

Figure 10:
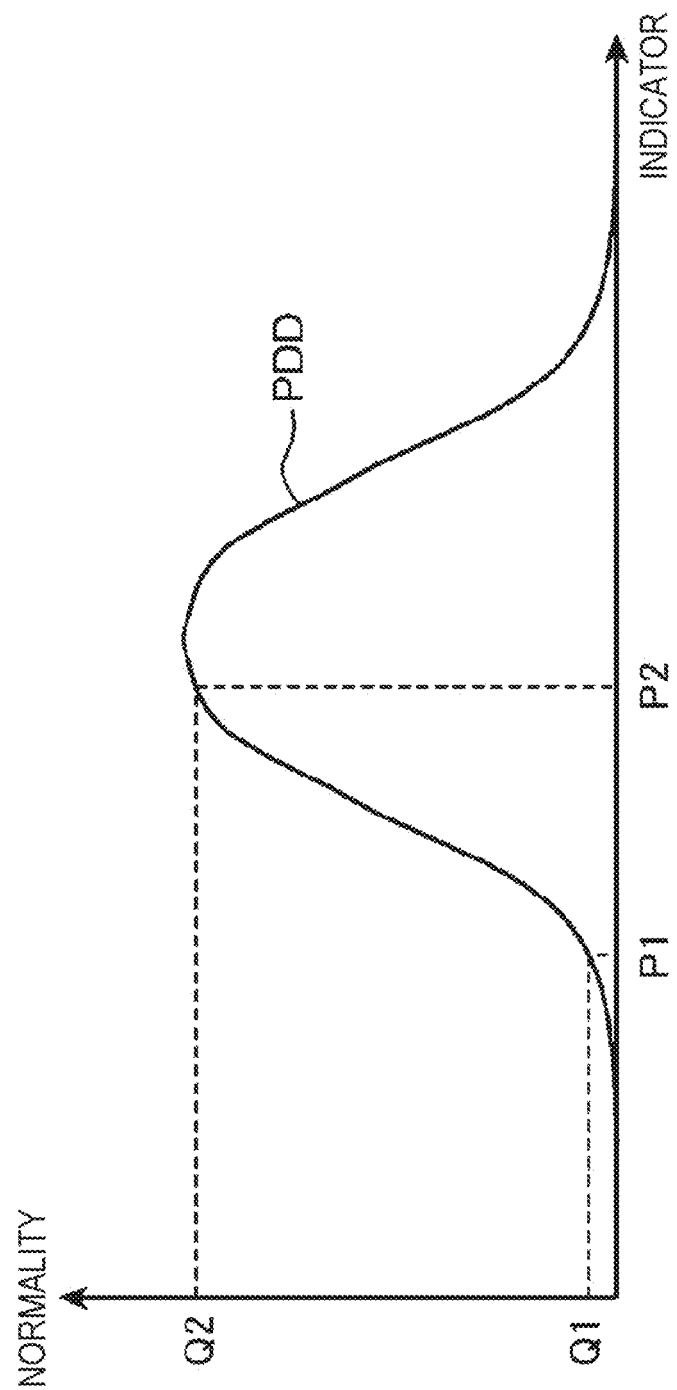
FIG. 10 is a diagram schematically illustrating a probability density distribution, which is an example of a normal model.

FIG. 10 is a diagram schematically illustrating a probability density distribution PDD, which is an example of a normal model. When an indicator extracted from a structure is one-dimensional, for example, the structure abnormality determination unit 102 determines whether the structure is in an abnormal state using a probability density distribution PDD such as that illustrated in FIG. 10. The structure abnormality determination unit 102 determines a level of normality of a target indicator extracted from a structure on the basis of a probability in a probability density distribution PDD of an indicator in a normal model, corresponding to the target indicator. In FIG. 10, for example, levels of normality of extracted indicators P1 and P2 are Q1 and Q2, respectively. The structure abnormality determination unit 102 then determines that the indicator P2 is likely to be normal and that the indicator P1 is likely to be abnormal.

A method for representing the probability density distribution PDD may be a method in which a parametric model based on a relatively small number of parameters is used, a method in which a non-parametric model for identifying a shape of distribution using individual data without assuming a certain function type is used, or the like. When an indicator extracted from a structure is in low dimensions, the structure abnormality determination unit 102 determines whether the structure is in an abnormal state using the probability density distribution. When a parametric model is used, for example, parameters indicating a probability density distribution (e.g., an average and a standard deviation of normal distribution) are stored in the normal model storage unit 103 as a normal model. When an indicator extracted from a structure is in high dimensions, such as in the case of an image, on the other hand, a method for determining an abnormality based on dimension reduction may be used.

Figure 11:
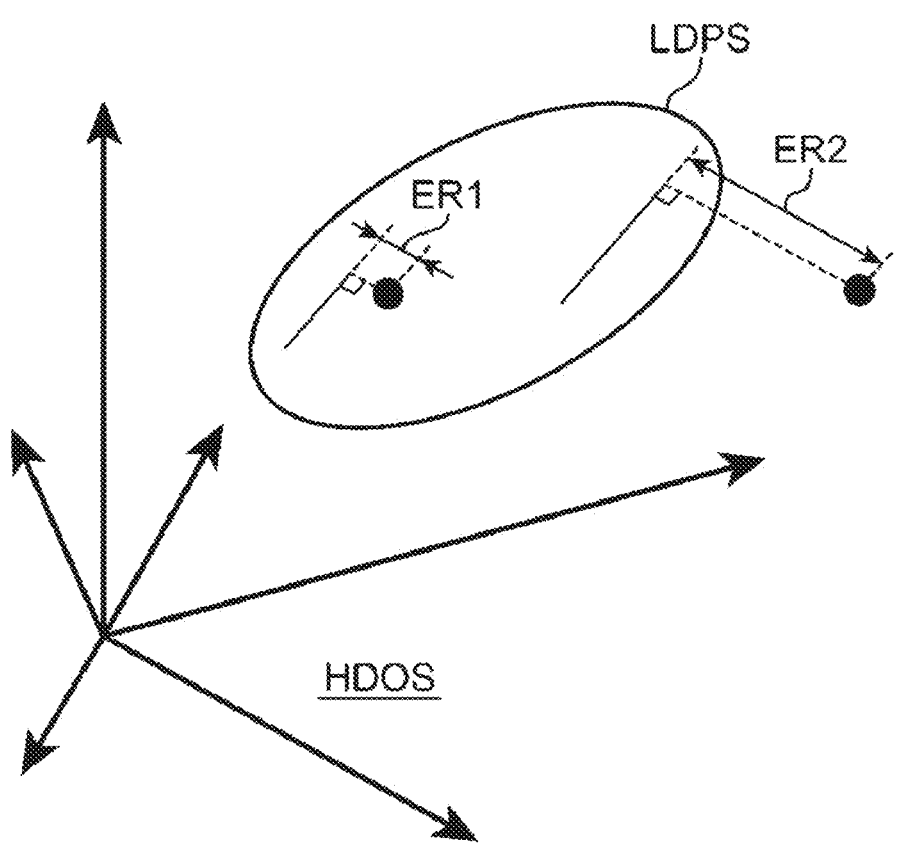
FIG. 11 is a diagram illustrating a method for controlling display of an abnormality based on dimension reduction.
Figure 12:
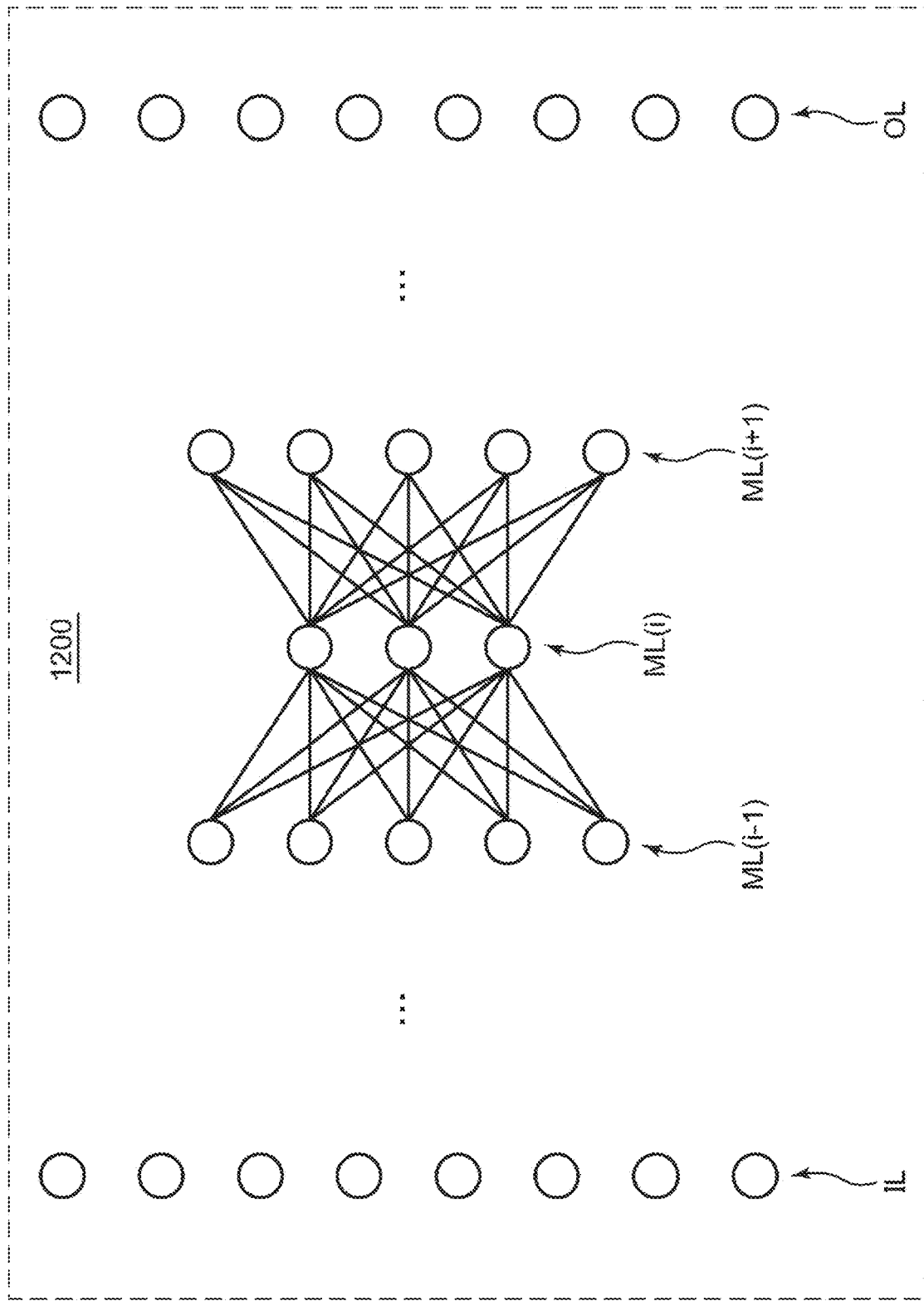
FIG. 12 is a diagram illustrating the network configuration of a multilayer autoencoder.

FIG. 11 is a diagram illustrating a method for determining an abnormality that uses a reconstruction error at a time of dimension reduction. Before machine learning for constructing a normal model, a low-dimensional subspace LDPS is obtained by reducing dimensions of a high-dimensional original space HDOS in which a learning data set is distributed. When the low-dimensional subspace LDPS is obtained while constructing the learning data set only with normal data, the obtained low-dimensional subspace LDPS is expected to reflect features of the normal data. When an indicator extracted from a structure is projected onto the low-dimensional subspace LDPS, a reconstruction error ER1 smaller than a certain threshold is obtained if features of the indicator are similar to those of the original learning data (i.e., in the case of normal data). In the case of abnormal data, on the other hand, a reconstruction error ER2 equal to or larger than the certain threshold is obtained. The structure abnormality determination unit 102 determines whether a structure is in an abnormal state using this characteristic. A reconstruction error can be calculated from a distance between a vector obtained by projecting an indicator extracted from a structure onto a low-dimensional subspace LDPS (i.e., obtained as a result of dimension compression) and a vector in an high-dimensional original space HDOS. For the dimension reduction, a method such as a principal component analysis, a multilayer autoencoder, or variational autoencoder may be used. FIG. 12 is a diagram illustrating the network configuration of a multilayer autoencoder 1200. As illustrated in FIG. 12, the multilayer autoencoder 1200 is an hourglass feedforward network that includes an input layer IL, an output layer OL, and two or more intermediate layers ML, where neurons in each intermediate layer ML are fewer than in the input layer IL or the output layer OL. The multilayer autoencoder 1200 uses itself as training data so that outputs reproduce inputs. After the learning, the intermediate layers ML appropriately express features of the learning data set. Outputs of an intermediate layer ML(i), therefore, may be used as dimension reduction data.

Figure 13:
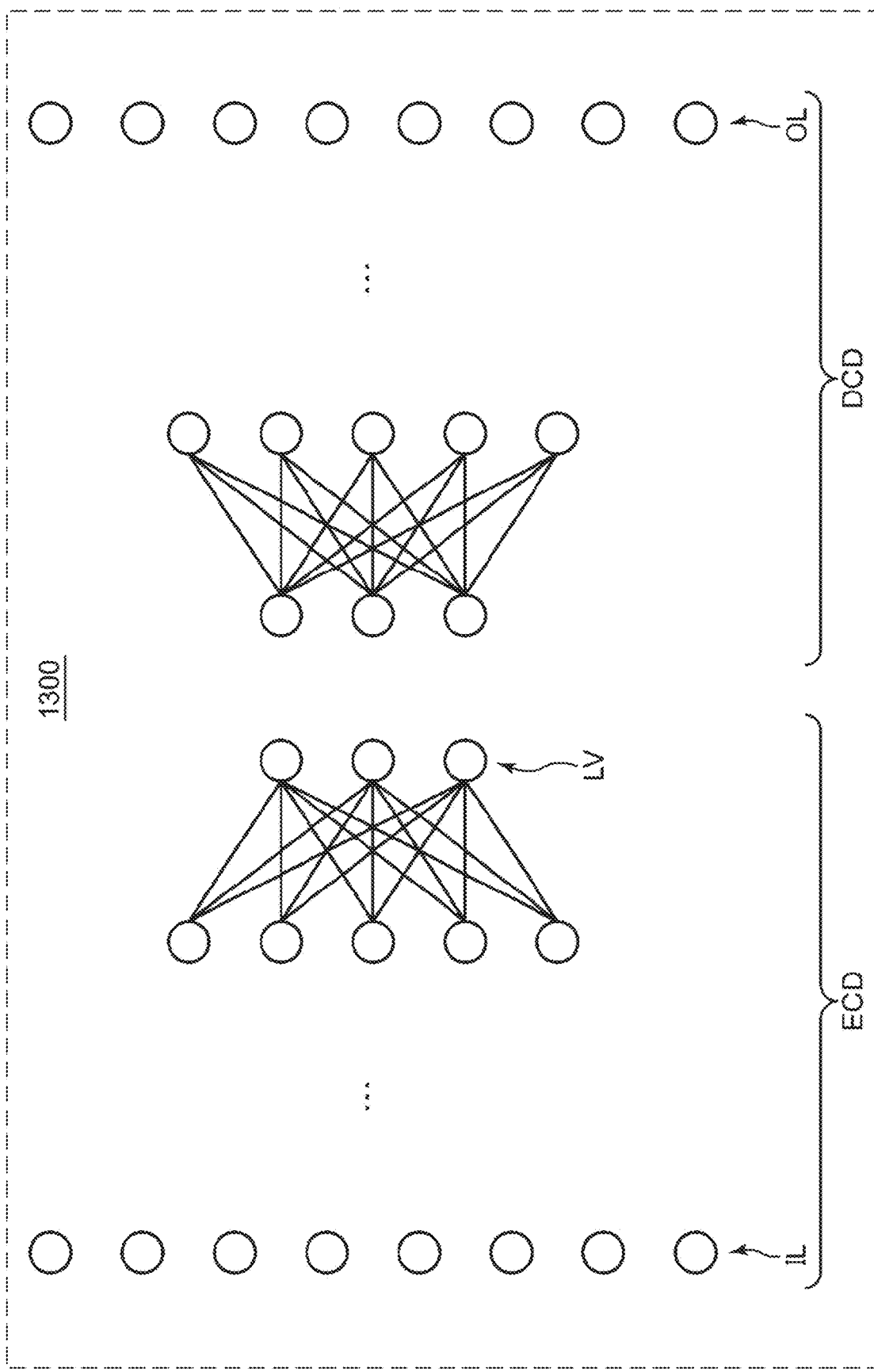
FIG. 13 is a diagram illustrating the network configuration of a variational autoencoder.

FIG. 13 is a diagram illustrating the network configuration of a variational autoencoder 1300. As illustrated in FIG. 13, the variational autoencoder 1300 is an hourglass network that includes an input layer IL, an output layer OL, and two or more intermediate layers, where, as with the multilayer autoencoder 1200 (FIG. 12), neurons in each intermediate layer are fewer than in the input layer IL or the output layer OL. Jinwon An and Sungzoon Cho, "Variational Autoencoder based Anomaly Detection Using Reconstruction Probability", Dec. 27, 2015, SNU Data Mining Center, 2015-2, Special Lecture on IE, for example, discloses a variational autoencoder. FIG. 13 corresponds to FIG. 2 or 3 of this example of the related art.

In the variational autoencoder 1300, an encoder ECD receives an image x and outputs parameters of a distribution $q\varphi(z|x)$ of z, which is a latent variable LV for generating the image x. A decoder DCD outputs a distribution $p\theta(x|z)$ of the generated image on the basis of z sampled from the distribution $q\varphi(z|x)$. Learning based on the variational autoencoder 1300 is performed by maximizing a variational lower bound of a logarithmic marginal likelihood $\log p\theta(x)$ of each point x of the data set. In the above example of the related art, a learning algorithm is described as algorithm 3.

An abnormality determination employing the variational autoencoder 1300 is performed as follows. A target chest X-ray image y is input to the encoder ECD subjected to machine learning, and a distribution $f(z|y)$ whose latent variable LV is z is obtained. The latent variable z is then obtained by performing sampling from this distribution, and a likelihood $p\theta(y|z)$ of the target chest X-ray image y is obtained using the obtained latent variable z. The structure abnormality determination unit 102 then determines whether a structure is abnormal or normal on the basis of the likelihood $p\theta(y|z)$. In the above example of the related art, a determination algorithm is described as algorithm 4.

In the case of the principal component analysis, a matrix to be subjected to dimension reduction is stored in the normal model storage unit 103 as a normal model. In the case of a multilayer autoencoder or a variational autoencoder, a network structure subjected to machine learning and parameters are stored in the normal model storage unit 103 as a normal model.

The method for determining whether a structure is in a normal state or an abnormal state used in common between steps S201 to S207 has been described. A specific method actually performed to achieve each step will be described hereinafter.

In step S201 illustrated in FIG. 8A, the structure abnormality determination unit 102 determines whether a position of the structure is normal. If the structure abnormality determination unit 102 determines that the position of the structure is abnormal (NO in step S201), the process proceeds to step S211. If the structure abnormality determination unit 102 determines that the position of the structure is normal (YES in S201), on the other hand, the process proceeds to step S212. After step S211 or S212, the process proceeds to step S202.

In preparation for step S201, a large number of binary mask images, such as those illustrated in FIGS. 4B, 5B, and 6B, are prepared for learning. Coordinates (GXpj, GYpj) of the center of gravity of a mask area are calculated for each structure Pp or each sample j, and these two-dimensional coordinates of the center of gravity are used as an indicator for determining whether the structure is in a normal state or an abnormal state. A two-dimensional probability density distribution of the coordinates (GXpj, GYpj) of the centers of gravity calculated from the binary mask images for learning is obtained and stored in the normal model storage unit 103 in advance as a normal model.

Alternatively, in order to absorb misalignment at a time of capture of an image by the chest X-ray image capture apparatus 300 and differences in the size of a subject, a bone (a rib, a thoracic vertebra, etc.) that is not easily affected by a disease compared to a lung field and by an attitude of the subject at the time of the capture of the image may be detected and normalized to a standard position and a standard size. Normalized coordinates (NGXpj, NGYpj) of the center of gravity may then be obtained and stored in the normal model storage unit 103 in advance as a normal model.

Figure 14A:
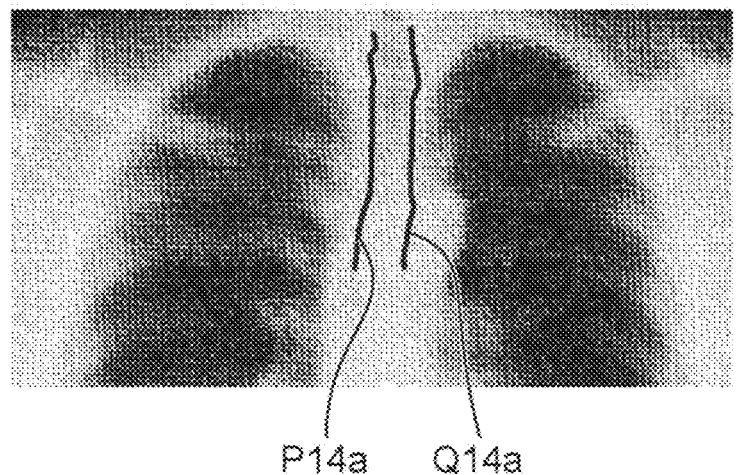
FIG. 14A is a diagram illustrating an example in which positions of structures are normal.
Figure 14B:
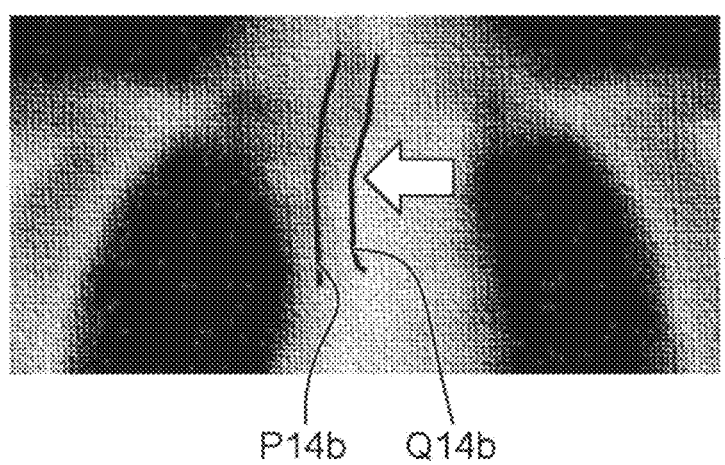
FIG. 14B is a diagram illustrating an example in which positions of structures are abnormal.

The structure abnormality determination unit 102 calculates coordinates of the center of gravity from a mask image of a structure Pp detected by and output from the structure detection unit 101. The structure abnormality determination unit 102 makes an abnormality determination by comparing the calculated coordinates of the center of gravity with the two-dimensional probability density distribution, which is stored in the normal model storage unit 103, corresponding to the structure Pp. FIGS. 14A and 14B illustrate examples of an abnormality that can be determined.

FIGS. 14A and 14B are diagrams illustrating examples in which the left and right walls of the trachea are defined as structures. FIG. 14A illustrates an example in which a structure P14a (an example in which a structure is a combination of a first linear area and a second linear area) corresponding to the right wall of the trachea and a structure Q14a (an example of the first linear area) corresponding to the left wall of the trachea are located at normal positions. FIG. 14B illustrates an example in which a structure P14b corresponding to the right wall of the trachea and a structure Q14b corresponding to the left wall of the trachea has shifted to the right (to the left in the image) relative to the body due to a disease.

In the present embodiment, the left and right walls of the trachea are defined as structures including a linear structure. That is, most of the trachea is inside the mediastinum, and bronchial walls in this part are examples of the first linear area. When the trachea or a bronchus becomes adjacent to the left lung field near a point at which the trachea bifurcates into the bronchi, a right wall of the trachea or the bronchus is an example of the second linear area. The left wall of the trachea, on the other hand, is an example of the first linear area since the descending aorta exists near the point at which the trachea bifurcates into the bronchi. Alternatively, an area occupied by the trachea may be defined as an area structure.

In step S202 illustrated in FIG. 8A, the structure abnormality determination unit 102 determines whether an angle between the structure and another structure is normal. If the structure abnormality determination unit 102 determines that the angle is abnormal (NO in step S202), the process proceeds to step S221. If the structure abnormality determination unit 102 determines that the angle is normal (YES in step S202), the process proceeds to step S222. After step S221 or S222, the process proceeds to step S203.

The abnormality determination in step S202 as to an angle is performed on a tracheal bifurcation angle, which is an angle at a position at which the bronchi diverge, a rib diaphragm angle, or the like.

Figure 15:
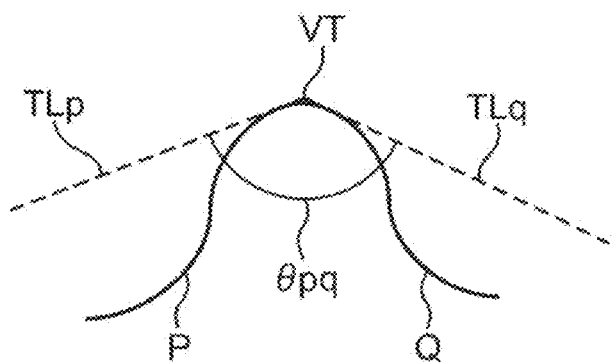
FIG. 15 is a diagram illustrating calculation of an angle between two linear structures.

FIG. 15 is a diagram illustrating calculation of angle between two linear structures P and Q that make an angle with each other. When an angle is used for an abnormality determination, two linear structures P and Q that make an angle with each other are used as structures as illustrated in FIG. 15. A large number of binary mask images of the two linear structures P and Q that make an angle with each other are prepared in advance. A vertex VT of the two linear structures P and Q is then calculated for each sample j. A tangential line TLp to the linear structure P and a tangential line TLq to the linear structure Q are calculated near the vertex VT, and an angle θpq between the tangential lines TLp and TLq is calculated. The angle θpq is used as an indicator for making a determination as to a normal state or an abnormal state. A one-dimensional probability density distribution of angles θpq calculated from the binary mask images for learning in this manner is obtained and stored in the normal model storage unit 103 in advance as a normal model.

Here, a method for calculating the vertex Vt, the tangential line TLp to the linear structure P, and the tangential line TLq to the linear structure Q from the two linear structures P and Q will be described with reference to FIG. 33. A-1 of FIG. 33 illustrates a chest X-ray image (trimmed around an area necessary for description) to be processed, and A-2 of FIG. 33 illustrates an image obtained by cutting out an area R1 illustrated in A-1 of FIG. 33 and performing contrast adjustment in the area R1 so that the trachea can be visually recognized. A-3 of FIG. 33 illustrates an image including areas PA3 and QA3, which are obtained by performing area extraction on the linear structures P and Q, respectively, illustrated in FIG. 15. An angle θpq in FIG. 15 is a tracheal bifurcation angle, which is an angle by which the trachea bifurcates, on the chest X-ray image, and a point VT is a vertex of the tracheal bifurcation angle. Since the bronchi diverge to the left and right from the downward trachea and enter the left and right lungs, normal bronchi are drawn in a chest X-ray image as gentle curves slightly protruding downward as illustrated in FIG. 33. Tangential lines to the linear structures P and Q from the vertex VT can therefore be obtained by performing straight line approximation on parts of the linear structures P and Q near the vertex VT. Although the linear structures P and are lower boundaries of the left and right bronchi, ranges of P and Q from the vertex VT used in learning for U-Net may be determined by a designer. In a present case, P and Q are determined as lower boundaries of the left and right bronchi overlapping a central shadow (a central part of the chest X-ray image where X-ray is significantly absorbed) including the thoracic vertebrae and the descending aorta. As the parts of the linear structures P and Q near the vertex VT, the central one-third of the linear structures P and Q is used. As described above, some linear structures are wider than one pixel in an image, and therefore the two linear structures P and Q are thinned down. A thinning algorithm may be one proposed by Zhang-Suen, Tamura, Nagendraprasad-Wang-Gupta, or Hilditch, for example, but any method may be used. The Zhang-Suen thinning algorithm, which is a relatively high-speed method, for example, may be used. A-4 of FIG. 33 illustrates areas PA4 and QA4, which are connection components that are one pixel wide, obtained by thinning down the areas PA3 and QA3 illustrated in A-3 of FIG. 33. Next, as illustrated in A-5 of FIG. 33, areas PA5 and QA5, which are the central one-third (the number of pixels connected to one another) of the areas PA4 and QA4, respectively, in the image, are obtained. Next, the areas PA5 and QA5 are subjected to straight line approximation using a method such as a Hough transform. The angle θpq can be calculated using expressions of two straight lines obtained as a result of the straight line approximation.

Figure 16A:
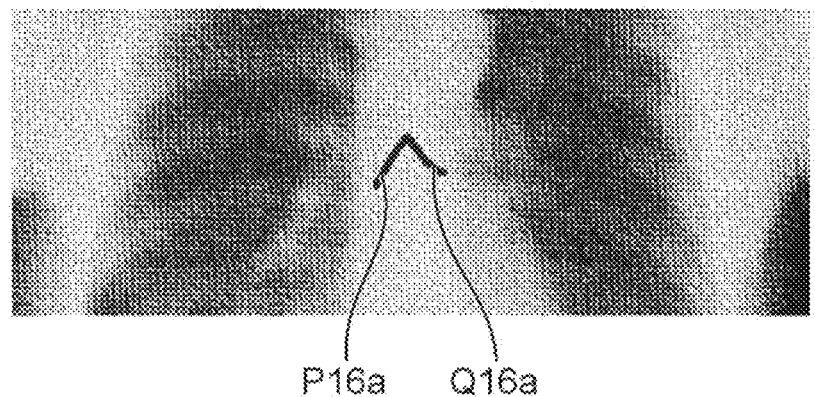
FIG. 16A is a diagram illustrating an example in which an angle between two linear structures is normal.
Figure 16B:
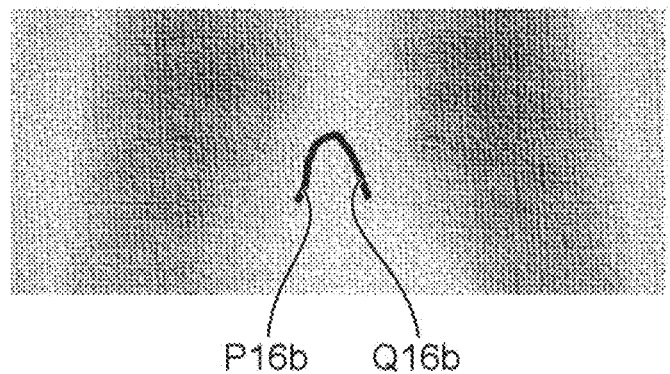
FIG. 16B is a diagram illustrating an example in which an angle between two linear structures is abnormal.

Although the linear structures P and Q are separate from each other in FIG. 33 unlike in FIGS. 15, 16A, and 16B, the above method can be used regardless of whether the linear structures P and Q are connected to each other or separate from each other.

The structure abnormality determination unit 102 calculates an angle between mask images of the linear structures P and Q detected by and output from the structure detection unit 101. The structure abnormality determination unit 102 makes an abnormality determination by comparing the calculated angle with the one-dimensional probability density distribution corresponding to the linear structures P and Q saved in the normal model storage unit 103. FIGS. 16A and 16B illustrate examples of an abnormality that can be determined.

FIGS. 16A and 16B are diagrams illustrating examples in which two lower boundary lines of a diverging part of the bronchi are defined as linear structures. FIG. 16A illustrates an example in which a tracheal bifurcation angle between a linear structure P16a (an example of the first linear area) and a linear structure Q16a (an example of the first linear area) is normal. FIG. 16B illustrates an example in which a tracheal bifurcation angle between a linear structure P16b (an example of the first linear area) and a linear structure Q16b (an example of the first linear area) has increased due to a disease.

In step S203 illustrated in FIG. 8A, the structure abnormality determination unit 102 determines whether a distance between the structure and another structure is normal. If the structure abnormality determination unit 102 determines that the distance is abnormal (NO in step S203), the process proceeds to step S231. If the structure abnormality determination unit 102 determines that the distance is normal (YES in step S203), the process proceeds to step S232. After step S231 or S232, the process proceeds to step S204.

When a distance is used for an abnormality determination, two structures are used. A large number of binary mask images, such as those illustrated in FIGS. 4B, 5B, and 6B, are prepared in advance for learning. A distance Dpqj between a mask image of a structure Pp and a mask image of a structure Qq is calculated for each pair of structures Pp and Qq for which a distance is to be obtained and for each sample j. This distance is used as an indicator for making a determination as to a normal state or an abnormal state. A one-dimensional probability density distribution of distances Dpqj calculated from the binary mask images for learning in this manner is obtained and stored in the normal model storage unit 103 in advance as a normal model.

Figure 17A:
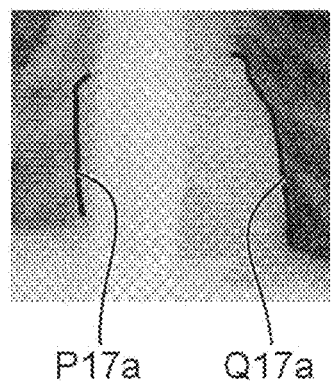
FIG. 17A is a diagram illustrating an example in which a distance between two linear structures is normal.
Figure 17B:
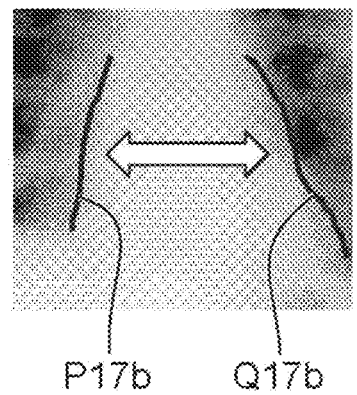
FIG. 17B is a diagram illustrating an example in which a distance between two linear structures is abnormal.

The structure abnormality determination unit 102 calculates a distance from the mask images of the structures Pp and Qq detected by and output from the structure detection unit 101. The structure abnormality determination unit 102 makes an abnormality determination by comparing the calculated distance with the one-dimensional probability density distribution corresponding to the structures Pp and Qq saved in the normal model storage unit 103. As the distance, a distance between the center of gravity of the structure Pp and the center of gravity of the structure Qq may be used. FIGS. 17A and 17B illustrate examples of an abnormality that can be determined.

FIGS. 17A and 17B are diagrams illustrating examples in which left and right boundary lines of a heart shadow are defined as linear structures. FIG. 17A illustrates an example in which a distance between a linear structure P17a (an example of the first linear area) of the right heart shadow and a linear structure Q17a (an example of the first linear area) of the left heart shadow is normal. FIG. 17B illustrates an example in which a distance between a linear structure P17b (an example of the first linear area) of the right heart shadow and a linear structure Q17b (an example of the first linear area) of the left heart shadow has been increased due to a disease. One or both of two linear structures that define a distance can be determined to be in an abnormal state in the abnormality determination in step S201 as to a position.

In step S204 illustrated in FIG. 8A, the structure abnormality determination unit 102 determines whether the area of the structure is normal. IF the structure abnormality determination unit 102 determines that the area is abnormal (NO in step S204), the process proceeds to step S241. If the structure abnormality determination unit 102 determines that the area is normal (YES in step S204), the process proceeds to step S242. After step S241 or S242, the process proceeds to step S205 (FIG. 8B).

A large number of binary mask images, such as those illustrated in FIGS. 4B, 5B, and 6B, are prepared in advance for learning. Area Apj of a mask image is calculated for each structure Pp and for each sample j. This area is used as an indicator for making a determination as to a normal state or an abnormal state. A one-dimensional probability density distribution of areas Apj calculated from the binary mask images for learning in this manner is obtained and stored in the normal model storage unit 103 in advance as a normal model.

Figure 18A:
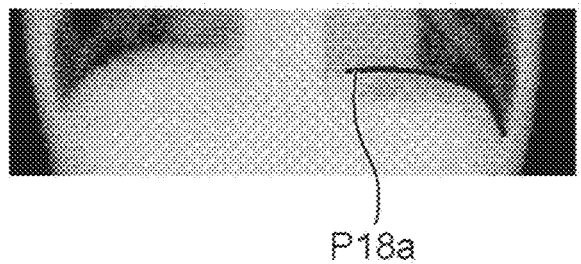
FIG. 18A is a diagram illustrating an example in which the area of a linear structure is normal.
Figure 18B:
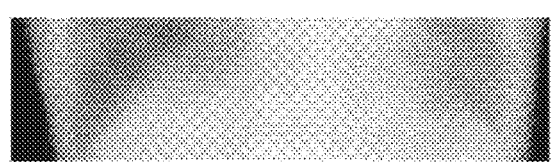
FIG. 18B is a diagram illustrating an example in which the area of the linear structure is abnormal.

The structure abnormality determination unit 102 calculates area from a mask image of a structure Pp detected by and output from the structure detection unit 101. The structure abnormality determination unit 102 makes an abnormality determination by comparing the calculated area with the one-dimensional probability density distribution corresponding to the structure Pp saved in the normal model storage unit 103. As the area, the area of pixels constituting the structure Pp may be used. Alternatively, the number of pixels constituting the structure Pp may be used as the area. FIGS. 18A and 18B illustrate examples of an abnormality that can be determined.

FIGS. 18A and 18B are diagrams illustrating examples in which a left (right in images) diaphragm dome shadow is defined as a linear structure. FIG. 18A illustrates an example in which a linear structure P18a (an example of the first linear area) corresponding to the diaphragm dome shadow is normal. FIG. 18B illustrates an example in which it has become difficult to visually recognize the linear structure corresponding to the diaphragm dome shadow due to a disease. In FIG. 18B, it is difficult for the structure detection unit 101 to detect a part or the entirety of a target structure (the diaphragm dome shadow here). The structure abnormality determination unit 102, therefore, can make an abnormality determination using the area of the structure detected by the structure detection unit 101 as an indicator.

In step S205 illustrated in FIG. 8B, the structure abnormality determination unit 102 determines whether the thickness (width) of the linear structure is normal. If the structure abnormality determination unit 102 determines that the thickness (width) is abnormal (NO in step S205), the process proceeds to step S251. If the structure abnormality determination unit 102 determines that the thickness (width) is normal (YES in step S205), on the other hand, the process proceeds to step S252. After step S251 or S252, the process proceeds to step S206.

A large number of binary mask images of linear structures, such as those illustrated in FIGS. 4B and 5B, are prepared in advance for learning. Width Wpj of a mask image is calculated for each linear structure P and for each sample j. This width is used as an indicator for making a determination as to a normal state or an abnormal state. A one-dimensional probability density distribution of widths Wpj calculated from the binary mask images for learning in this manner is obtained and stored in the normal model storage unit 103 in advance as a normal model.

Figure 19A:
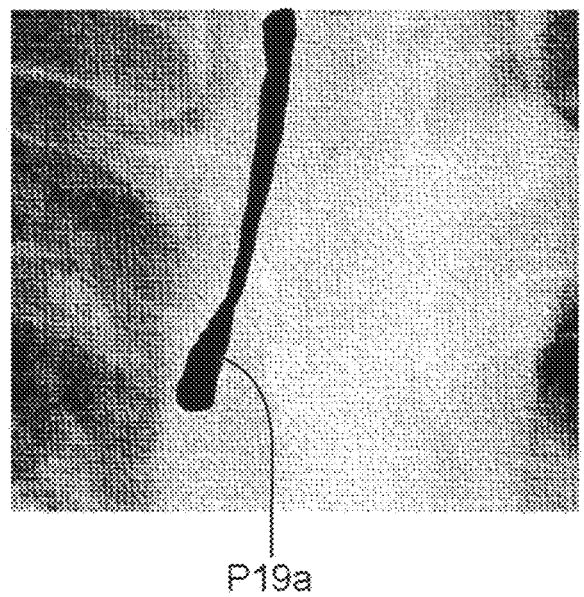
FIG. 19A is a diagram illustrating an example in which the width of a linear structure is normal.
Figure 19B:
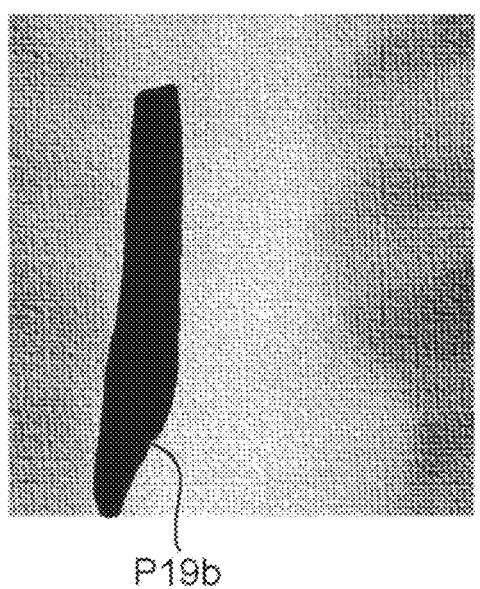
FIG. 19B is a diagram illustrating an example in which the width of a linear structure is abnormal.

The structure abnormality determination unit 102 calculates width from a mask image of a structure Pp detected by and output from the structure detection unit 101. The structure abnormality determination unit 102 makes an abnormality determination by comparing the calculated width with the one-dimensional probability density distribution corresponding to the structure Pp. A method for calculating width from a mask image may be a method in which a longitudinal direction and a lateral direction of a mask image of a linear structure are determined and an average, a mode, or a maximum value of the length in the lateral direction is determined as a width. FIGS. 19A and 19B illustrate examples of an abnormality that can be determined.

FIGS. 19A and 19B are diagrams illustrating examples in which a right (left in images) wall of the trachea is defined as a linear structure. FIG. 19A illustrates an example in which width of a linear structure P19a (an example of the second linear area) corresponding to the right wall of the trachea is normal. FIG. 19B illustrates an example in which a linear structure P19b (an example of the second linear area) corresponding to the right wall of the trachea has become wider (thicker) due to a disease.

In step S206 illustrated in FIG. 8B, the structure abnormality determination unit 102 determines whether an image pattern in an area sandwiched by the structure and another structure is normal. If the structure abnormality determination unit 102 determines that the image pattern is abnormal (NO in step S206), the process proceeds to step S261. If the structure abnormality determination unit 102 determines that the image pattern is normal (YES in step S206), the process proceeds to step S262. After step S261 or S262, the process proceeds to step S207.

When an image pattern in an area sandwiched by the structure and another structure is used for an abnormality determination, two structures are used in the present embodiment. A large number of binary mask images of structures (include linear structures), such as those illustrated in FIGS. 4B, 5B, and 6B, are prepared in advance for learning. An image Ipqj is cut out of an original image as an area sandwiched by structures for each sample j of structures Pp and Qq. The area of the image Ipqj cut out may be a circumscribed rectangle including both a mask image of the structure Pp and a mask image of the structure Qq. An area sandwiched by structures will be described with reference to FIGS. 20A to 20F.

Figure 20A:
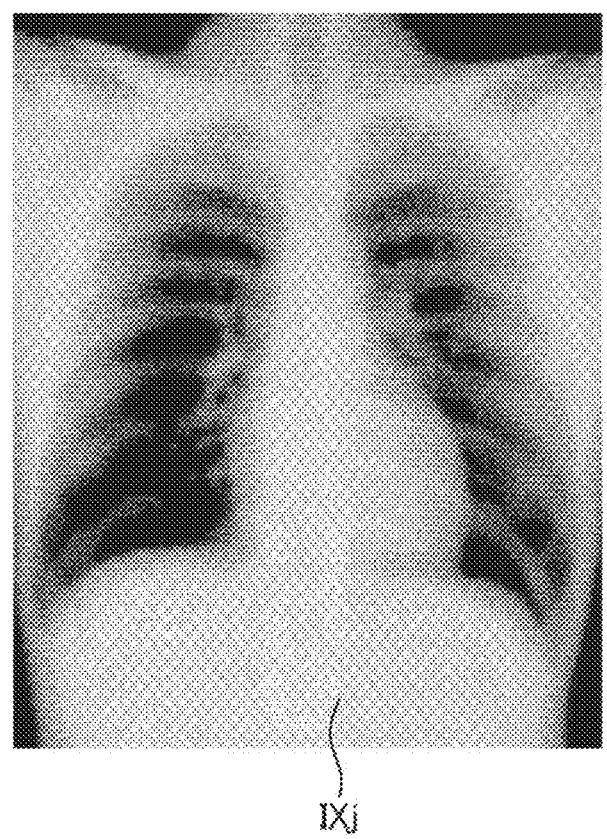
FIG. 20A is a diagram illustrating an image of a sample of a target chest X-ray image.
Figure 20B:
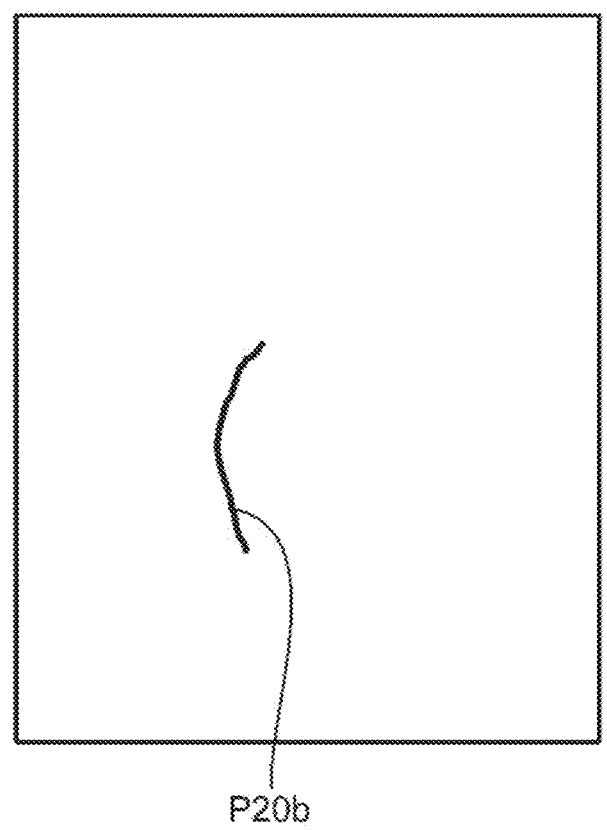
FIG. 20B is a diagram illustrating a mask image of a structure.
Figure 20C:
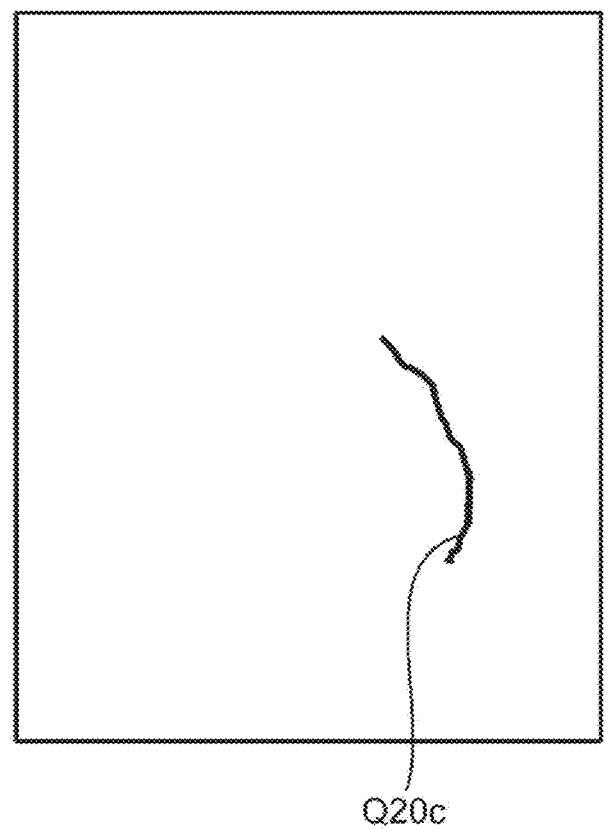
FIG. 20C is a diagram illustrating a mask image of another structure.
Figure 20D:
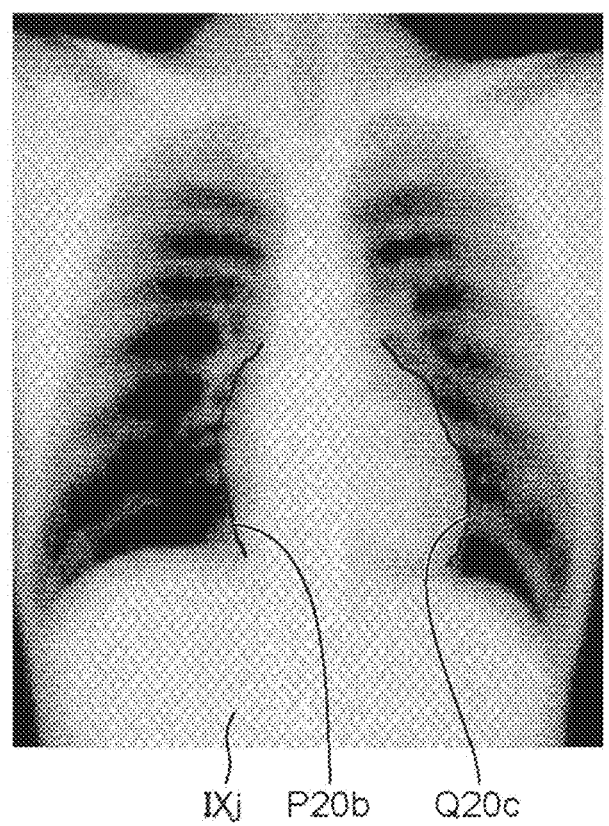
FIG. 20D is a diagram illustrating an image obtained by superimposing the mask images upon the target chest X-ray image.
Figure 20E:
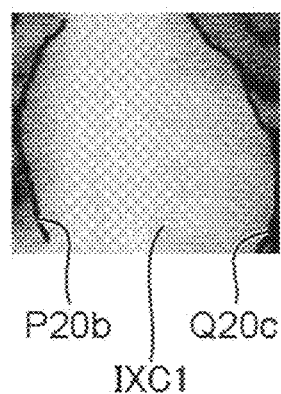
FIG. 20E is a diagram illustrating a cutout image upon which the mask images of the structures are superimposed.
Figure 20F:
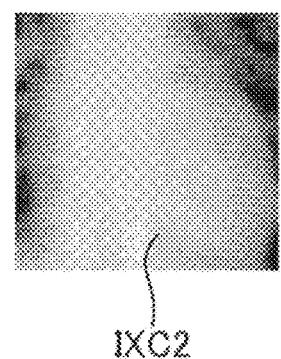
FIG. 20F is a diagram illustrating a cutout image upon which the mask images of the structures are not superimposed.

FIG. 20A is a diagram illustrating an image IXj of a sample j of a target chest X-ray image. FIG. 20B is a diagram illustrating a mask image of a structure P20b (an example of the first linear area) corresponding to FIG. 20A, FIG. 20C is a diagram illustrating a mask image of a structure Q20c (an example of the first linear area) corresponding to FIG. 20A. FIG. 20D is a diagram illustrating an image obtained by superimposing the mask images of the structures P20b and Q20c upon the image IXj of the sample j of the target chest X-ray image. FIG. 20E is a diagram illustrating, for the sake of description, a cutout image IXC1 upon which the mask images of the structures P20b and Q20c are superimposed. FIG. 20F is a diagram illustrating a cutout image IXC2 upon which the mask images of the structures P20b and Q20c are not superimposed, the cutout image IXC2 being an image to be actually used.

Figure 21A:
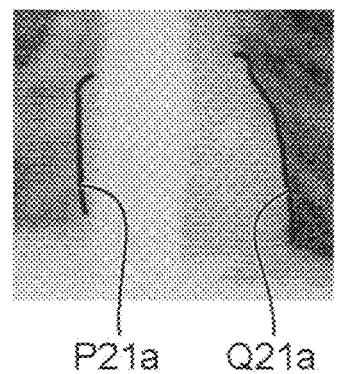
FIG. 21A is a diagram illustrating an example in which an area sandwiched by linear structures is normal.
Figure 21B:
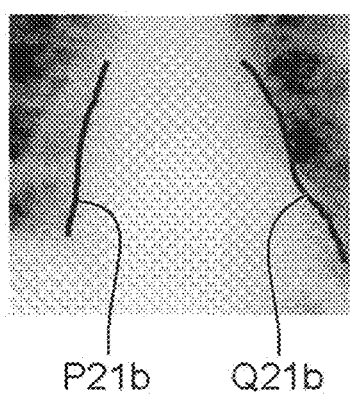
FIG. 21B is a diagram illustrating an example in which an area sandwiched by linear structures is abnormal.

As illustrated in FIG. 20F, after a local area of a target chest X-ray image is cut out, the structure abnormality determination unit 102 makes a determination as to an abnormal state using a reconstruction error at a time of dimension reduction, such as that illustrated in FIG. 11. FIGS. 21A and 21B illustrate examples of an abnormality that can be determined.

FIGS. 21A and 21B are diagrams illustrating examples in which a heart shadow is defined as an area sandwiched by a linear structure corresponding to a right heart shadow and a linear structure corresponding to a left heart shadow. FIG. 21A is a diagram illustrating an example in which a heart shadow sandwiched by a linear structure P21a (an example of the first linear area) corresponding to the right heart shadow and a linear structure Q21a (an example of the first linear area) corresponding to the left heart shadow is normal. In FIG. 21A, blood vessel shadows are seen on the heart shadow. FIG. 21B is a diagram illustrating an abnormal example in which blood vessel shadows are not seen on a heart shadow sandwiched by a linear structure P21b (an example of the first linear area) corresponding to the right heart shadow and a linear structure Q21b (an example of the first linear area) corresponding to the left heart shadow due to a disease overlapping the heart shadow.

In step S207 illustrated in FIG. 8B, the structure abnormality determination unit 102 determines whether an image pattern in a neighboring area of the structure is normal. If the structure abnormality determination unit 102 determines that the image pattern is abnormal (NO in step S207), the process proceeds to step S271. If the structure abnormality determination unit 102 determines that the image pattern is normal (YES in S207), the process proceeds to step S272.

A large number of binary mask images of structures (include linear structures), such as those illustrated in FIGS. 4B, 5B, and 6B, are prepared in advance for learning. An image Ipj is cut out of an original image as a neighboring area of a structure for each sample j of a structure Pp. The area of the cutout image Ipj may be a circumscribed rectangle of a mask image of the structure Pp. A neighboring area of a structure will be described with reference to FIGS. 22A to 22E.

Figure 22A:
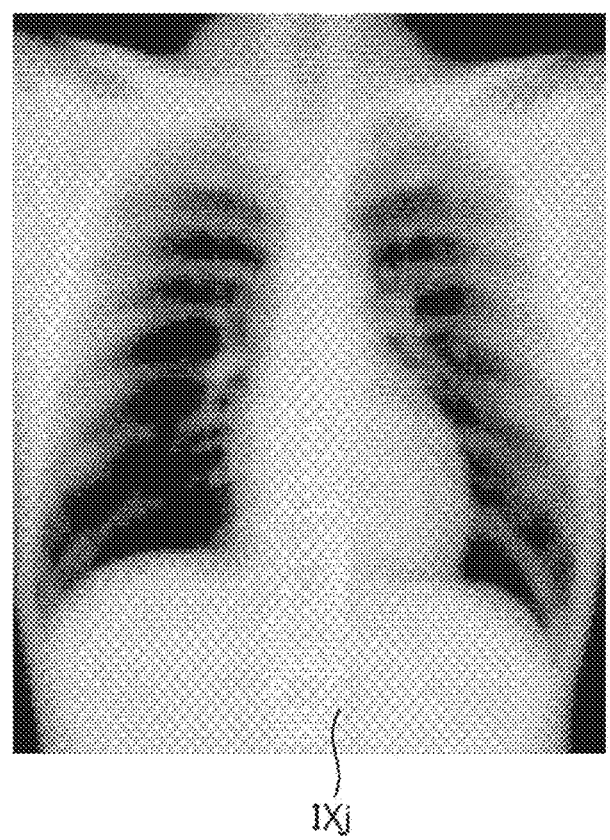
FIG. 22A is a diagram illustrating an image of a sample of a target chest X-ray image.
Figure 22B:
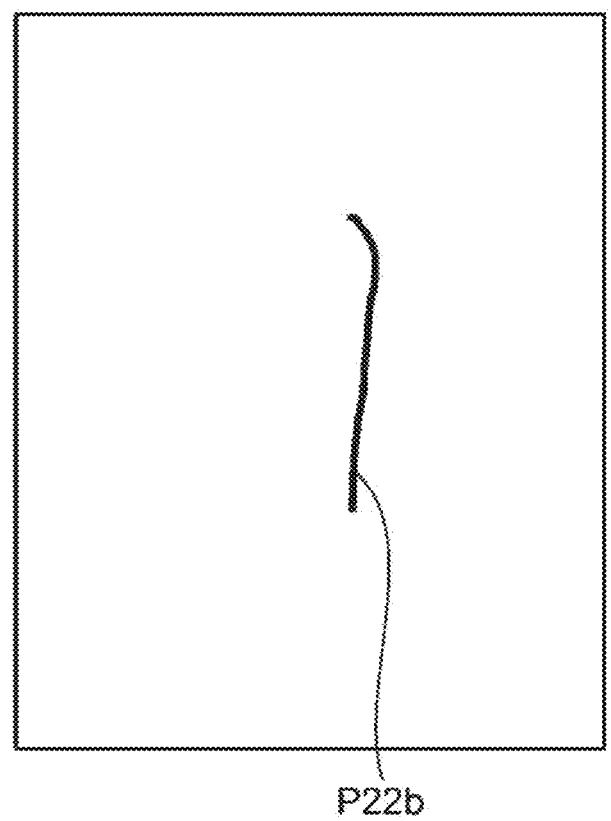
FIG. 22B is a diagram illustrating a mask image of a structure.
Figure 22C:
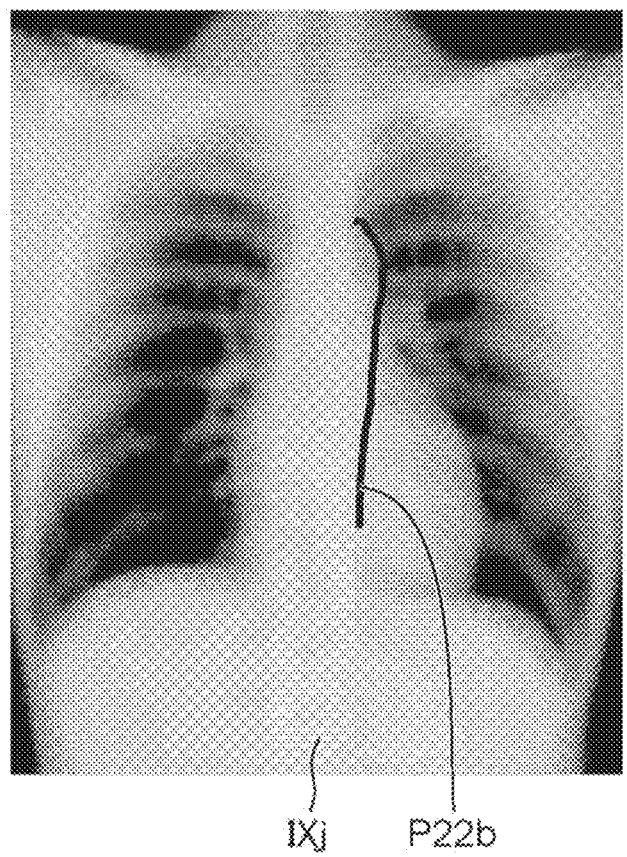
FIG. 22C is a diagram illustrating an image obtained by superimposing the mask image upon the target chest X-ray image.
Figure 22D:
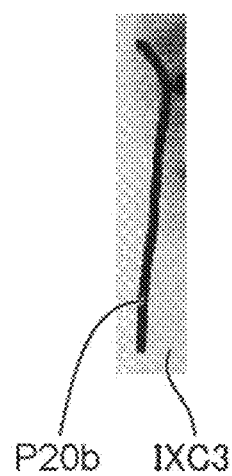
FIG. 22D is a diagram illustrating a cutout image upon which the mask image of the structure is superimposed.
Figure 22E:
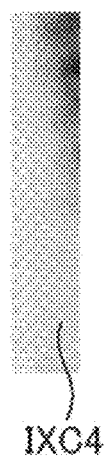
FIG. 22E is a diagram illustrating a cutout image upon which the mask image of the structure is not superimposed.

FIG. 22A is a diagram illustrating an image IXj of a sample j of a target chest X-ray image. FIG. 22B is a diagram illustrating a mask image of a structure P22b (an example of the first linear area) corresponding to FIG. 22A. FIG. 22C is a diagram illustrating an image obtained by superimposing a mask image of the structure P22b upon the image Ixj of the sample j of the target chest X-ray image. FIG. 22D is a diagram illustrating, for the sake of description, a cutout image IXC3 upon which the mask image of the structure P22b is superimposed. FIG. 22E is a diagram illustrating a cutout image IXC4 upon which the mask image of the structure P22b is not superimposed, the cutout image IXC4 being an image to be actually used.

As illustrated in FIG. 22E, after a local area of a target chest X-ray image is cut out, the structure abnormality determination unit 102 makes a determination as to an abnormal state using a reconstruction error at a time of dimension reduction, such as that illustrated in FIG. 11. An area cut out as a neighboring area of the structure P22b is not limited to a circumscribed rectangle of a mask image. For example, the area cut out as a neighboring area of the structure P22b may be an extended circumscribed rectangle of a mask image, instead, as illustrated in FIG. 22D. Alternatively, the area cut out as a neighboring area of the structure P22b may be an area obtained by extending an area of a mask image through an expansion process of a morphological operation. The morphological operation refers to a process for performing scanning while performing an convolutional operation on a certain kernel for an input image (binary). When a shape of 3×3 and an operation is performed once using a kernel whose values are all 1, for example, an output image (binary) expanded by one pixel can be obtained. In order to further expand the image, the kernel may be repeatedly used or a larger kernel may be used.

In step S211 illustrated in FIG. 8A, the structure abnormality determination unit 102 saves an abnormal result (i.e., a structure determined to be abnormal and details of the abnormality) to the memory 121. In step S212 illustrated in FIG. 8A, the structure abnormality determination unit 102 saves a normal result (i.e., a structure determined to be normal) to the memory 121.

In steps S221, S231, S241, S251, S261, and S271 illustrated in FIGS. 8A and 8B, as in step S211, the structure abnormality determination unit 102 saves an abnormal result (i.e., a structure determined to be abnormal and details of the abnormality) to the memory 121. In step S222, S232, S242, S252, S262, and S272 illustrated in FIGS. 8A and 8B, as in step S212, the structure abnormality determination unit 102 saves a normal result (i.e., a structure determined to be normal) to the memory 121. After step S271 or S272 illustrated in FIG. 8B, the process illustrated in FIGS. 8A and 8B (i.e., step S200 illustrated in FIG. 3) ends.

Steps S212, S222, S232, S242, S252, S262, and S272 illustrated in FIGS. 8A and 8B may be omitted. That is, the structure abnormality determination unit 102 may save only an abnormal result to the memory 121.

In step S300 illustrated in FIG. 3, the display control unit 122 displays a structure determined in step 3200 to be in an abnormal state and details of the abnormality in the structure on the display 108.

Figure 23:
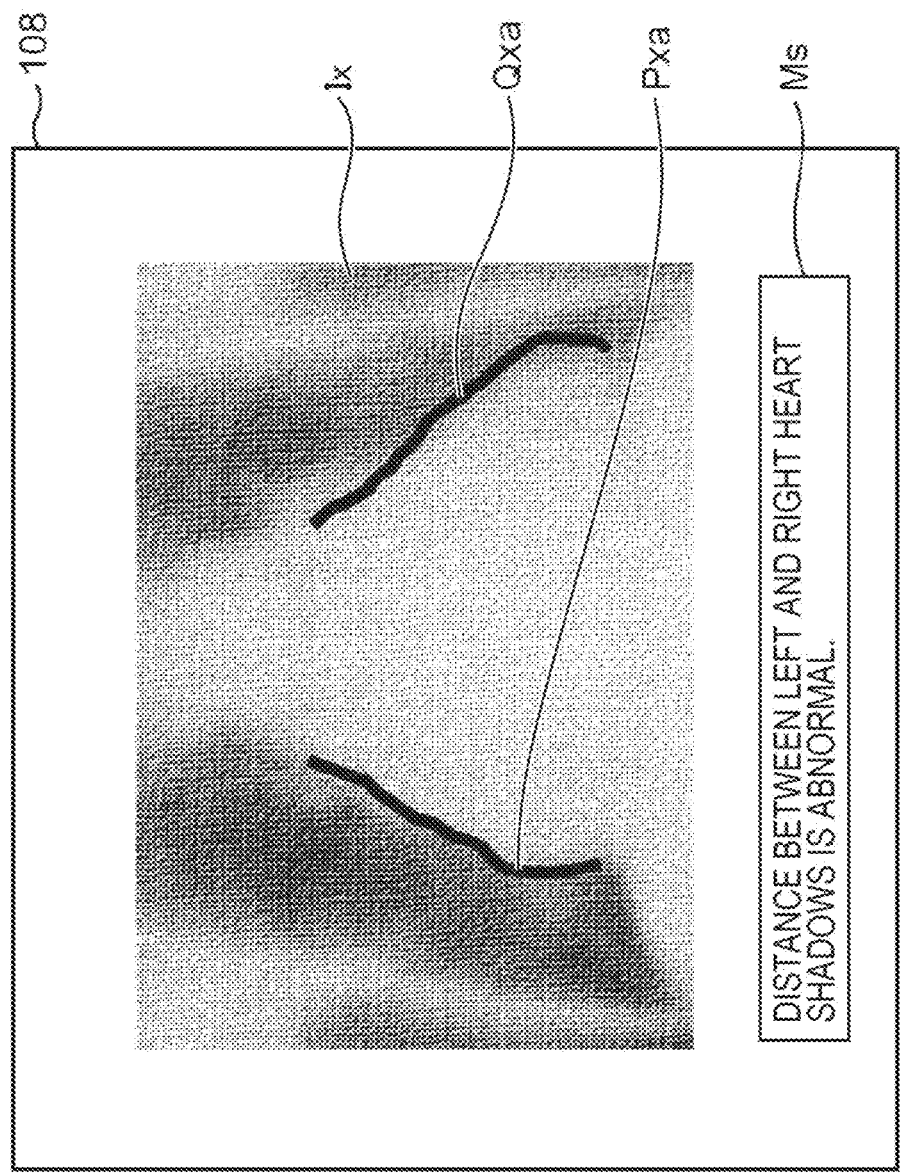
FIG. 23 is a diagram illustrating an example of a screen of a display according to the first embodiment.

FIG. 23 is a diagram schematically illustrating an example of a screen of the display 108. As illustrated in FIG. 23, the display control unit 122 displays a target chest X-ray image Ix, structures Pxa and Qxa determined to be in an abnormal state, and a message Ms indicating details of the abnormality in the structures Pxa and Qxa. Names of structures and messages Ms are defined in advance and saved in the memory 121.

As described above, according to the first embodiment of the present disclosure, various abnormalities in chest X-ray images can be determined with a unified framework, in which a structure including a linear structure formed of a first linear area that has been drawn by projecting anatomical structures whose X-ray transmittances are different from each other and that has a luminance different from a luminance in a surrounding area or a second linear area drawn by projecting an anatomical structure including a wall of the trachea or a bronchus or a hair line is detected using a model obtained in advance as a result of machine learning, an indicator for determining an abnormal state is calculated from the detected structure, the calculated indicator is compared with a predetermined reference value, whether the structure is in an abnormal state is determined on the basis of a result of the comparison, and the display 108 displays an area including the structure determined to be in an abnormal state and details of the abnormality in the structure.

In addition, not only a position of a detected lesion and/or a name of a disease but also information indicating how a certain structure is different from a normal state can be presented to a user, which is beneficial to the user. Not only an interpretation doctor but also a clinician or a radiologist, therefore, can give a diagnosis or study by himself/herself, or a medical student can be educated or study by himself/herself.

Second Embodiment

Figure 24:
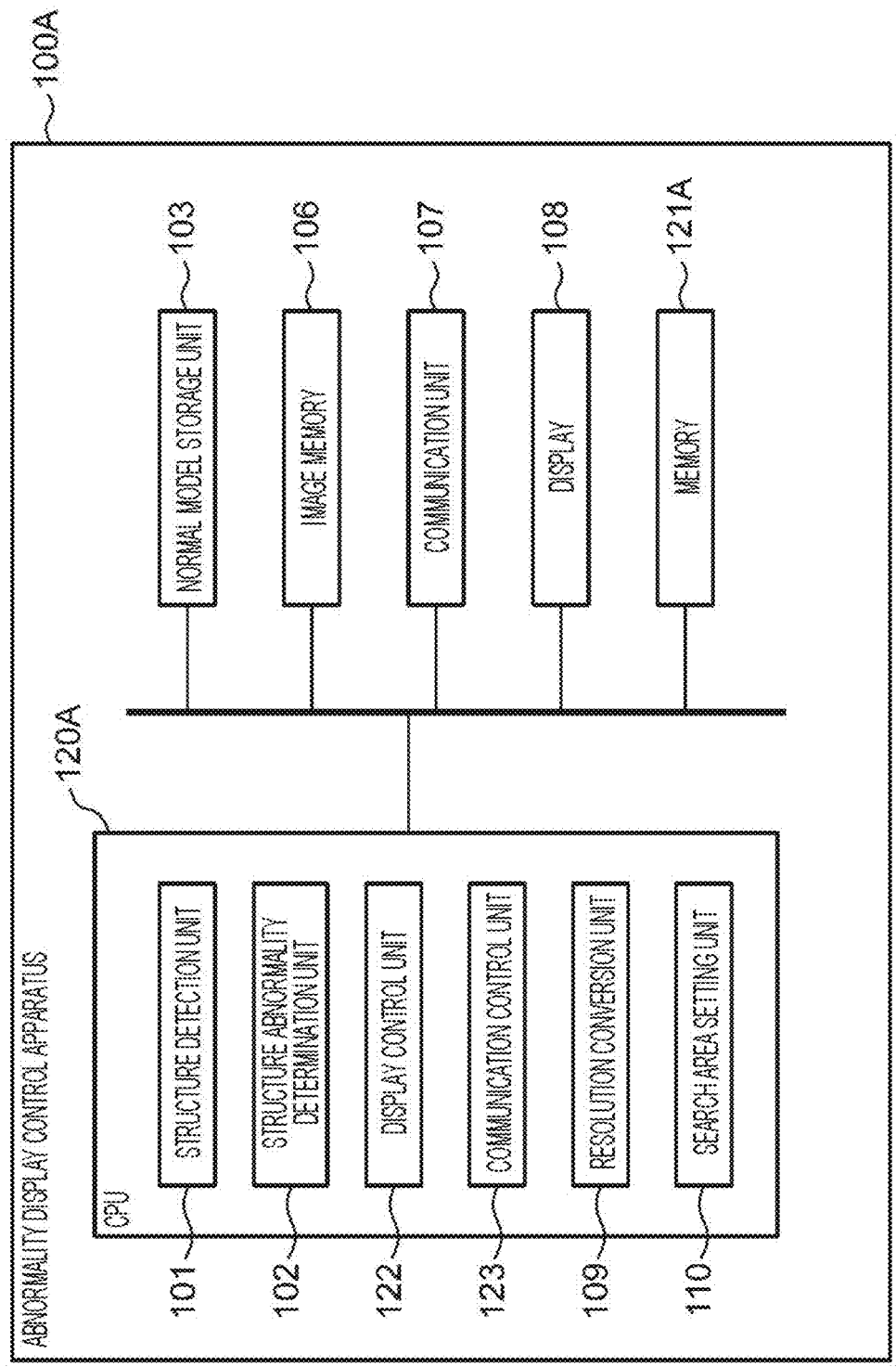
FIG. 24 is a block diagram illustrating the configuration of an abnormality display control apparatus according to a second embodiment.

FIG. 24 is a block diagram schematically illustrating the configuration of an abnormality display control apparatus 100A that performs a method for controlling display of an abnormality in a chest X-ray image according to a second embodiment. Unlike the abnormality display control apparatus 100 illustrated in FIG. 1, the abnormality display control apparatus 100A illustrated in FIG. 24 includes a CPU 120A instead of the CPU 120 and a memory 121A instead of the memory 121.

A normal model storage unit 103 (an example of a position memory) according to the second embodiment stores information regarding relative positional relationships between structures in advance. The memory 121A is configured in the same manner as the memory 121, and includes, for example, a ROM, a RAM, and an EEPROM. The ROM of the memory 121A stores a control program for operating the CPU 120A according to the second embodiment.

The CPU 120A executes the control program according to the second embodiment stored in the memory 121A to function as the structure detection unit 101, the structure abnormality determination unit 102, the display control unit 122, the communication control unit 123, a resolution conversion unit 109, and a search area setting unit 110.

The resolution conversion unit 109 creates images having different resolutions by performing reduction conversion of more than one stages on a target chest X-ray image. The resolution conversion unit 109 stores the created images in the image memory 106. The search area setting unit 110 sets an area to be searched for a structure on an image of a higher resolution using a result of detection of a structure performed by the structure detection unit 101 on a low-resolution image and information regarding a relative positional relationship between structures stored in the normal model storage unit 103.

Next, a process performed by the abnormality display control apparatus 100A according to the second embodiment will be described. The overall process is the same as in the first embodiment described with reference to the flowchart of FIG. 3.

Figure 25:
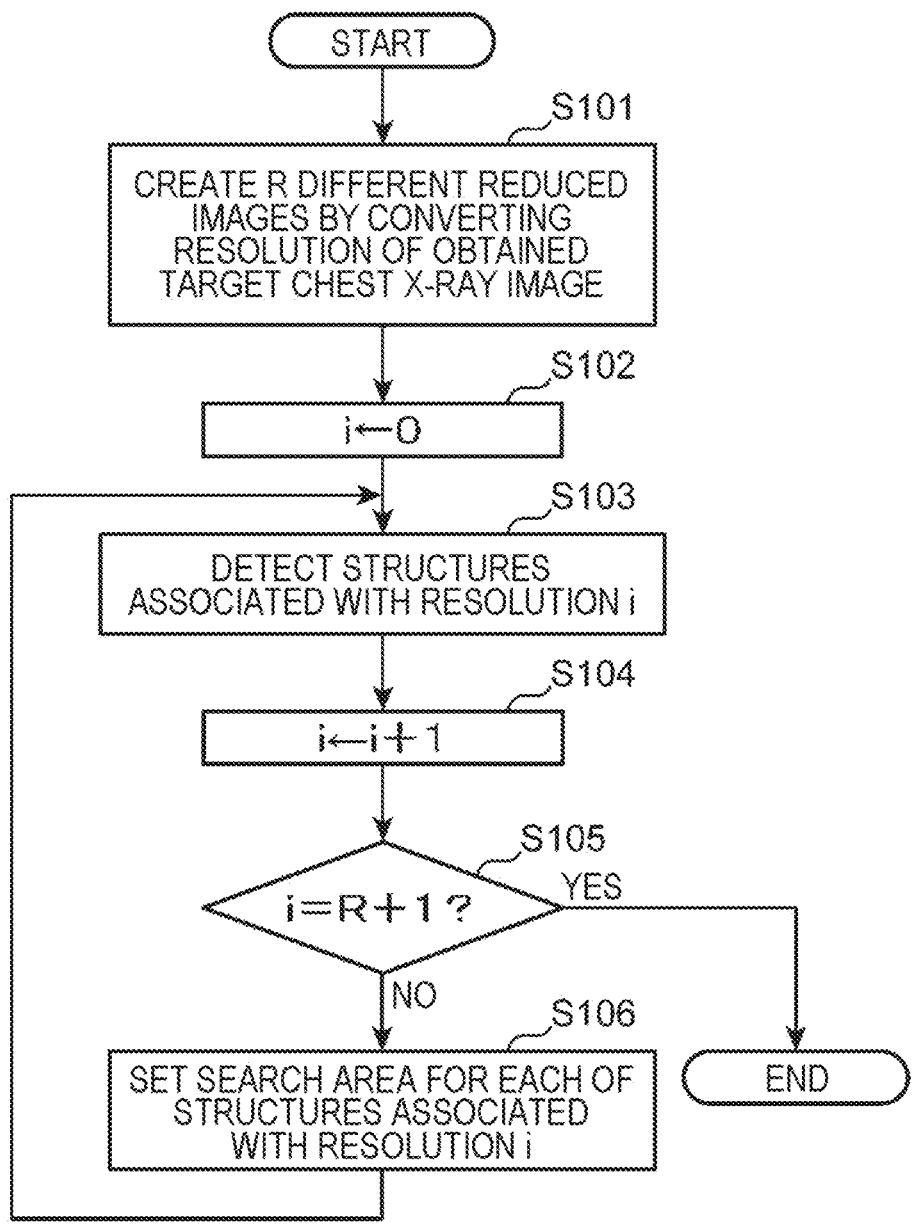
FIG. 25 is a flowchart illustrating a process for detecting a structure according to the second embodiment.

FIG. 25 is a flowchart schematically illustrating a process for detecting a structure performed by the abnormality display control apparatus 100A according to the second embodiment in step S100 (FIG. 3). FIG. 26 is a diagram schematically illustrating resolution information 2600.

In step S101 illustrated in FIG. 25, the resolution conversion unit 109 creates R (e.g., R=3 in the present embodiment) different reduced images for the target chest X-ray image obtained in step S50 (FIG. 3). The resolution of a chest X-ray image is usually 2,000 to 3,000 pixels each side. In the second embodiment, the resolution of the target chest X-ray image is, for example, 2,048×2,048. Resolutions of three different reduced images created by the resolution conversion unit 109 are, for example, 1,024×1,024, 512×512, and 256×256.

In the second embodiment, resolution i is set at 0, 1, 2, and 3 for the images in ascending order of resolution. That is, the resolution i of the 256×256 image is 0, the resolution i of the 512×512 image is 1, the resolution i of the 1,024×1,024 image is 2, and the resolution i of the 2,048×2,048 image (i.e., the original image) is 3. The resolution conversion unit 109 stores the created low-resolution reduced images in the image memory 106.

Next, in step S102, the structure detection unit 101 reads the image whose resolution i=0 (i.e., the lowest-resolution, namely, 256×256, image) from the image memory 106 as a structure detection target image. Next, in step S103, the structure detection unit 101 detects structures associated with the image of the resolution i (the image whose resolution i=0 in a first round of step S103) on the basis of the resolution information 2600 (FIG. 26).

As illustrated in FIG. 26, the resolution information 2600 includes a structure identifier (ID) field 2601 and a resolution i field 2602. In the structure ID field 2601, N structures whose structure IDs are 1 to N and that are defined in the first embodiment are set. In the resolution i field 2602, the resolution of an image to be used to detect a corresponding structure in the structure ID field 2601 is defined. A structure whose structure ID is 1, for example, is detected from the image whose resolution i is 0, that is, the 256×256 image. Although only one resolution is set for each structure in FIG. 26, the number of resolutions is not limited to this. For example, two or more resolution may be set depending on a structure, and the structure may be detected using images of the two or more resolutions.

As in the first embodiment, the structure detection unit 101 detects a structure using U-Net disclosed in "U-Net: Convolutional Networks for Biomedical Image Segmentation". As described above, U-net is a type of convolutional neural network. A convolutional neural network is a type of deep neural network. A neural network including two or more intermediate layers is called a deep neural network. During machine learning for a deep neural network and detection of a structure, processing speed is usually increased using a graphics processing unit (GPU). At this time, it might be difficult to handle a high-resolution image due to a restriction to the memory capacity of the GPU. In such a case, an image obtained by reducing an original image and decreasing the resolution of the original image is input to U-Net. In this case, however, detection performance for small structures, such as linear structures, can decrease. For this reason, in the second embodiment, the structure detection unit 101 detects a relatively large (an example of a first size) structure from a low-resolution image and a relatively small (an example of a second size) structure within a limited search area by trimming a high-resolution image.

In step S104 illustrated in FIG. 25, the structure detection unit 101 increments the resolution i. In a first round of step S104, i=1. In step S105, the structure detection unit 101 determines whether the resolution i has exceeded an upper limit (i.e., i=R+1) of resolution. If the resolution i has exceeded the upper limit of resolution (YES in step S105), the process illustrated in FIG. 25 ends, and step S100 (FIG. 3) ends. If the resolution i has not exceeded the upper limit of resolution (NO in step S105), the process proceeds to step S106.

In step S106, the search area setting unit 110 selects all structures associated with the resolution i (i=1 in a first round of step S106) on the basis of the resolution information 2600 illustrated in FIG. 26 and sets a search area for an image of the resolution i for each of the corresponding structures. A large number of binary mask images of structures, such as those illustrated in FIGS. 4B, 5B, and 6B, are prepared in advance for learning. Relative positional relationships between structures are obtained from the binary mask images for learning and stored in the normal model storage unit 103 (an example of the position memory) in advance. The search area setting unit 110 reads the relative positional relationships saved in the normal model storage unit 103 and uses the relative positional relationships to set search areas. After step S106 ends, the process returns to step S103. In a second round of step S103, the structure detection unit 101 detects structures associated with the image of the resolution i (the image whose resolution i=1 in the second step S103) on the basis of the resolution information 2600 (FIG. 26). Steps S103 to S106 are then repeated while the resolution i does not exceed the upper limit of resolution (NO in step S105).

Figure 27:
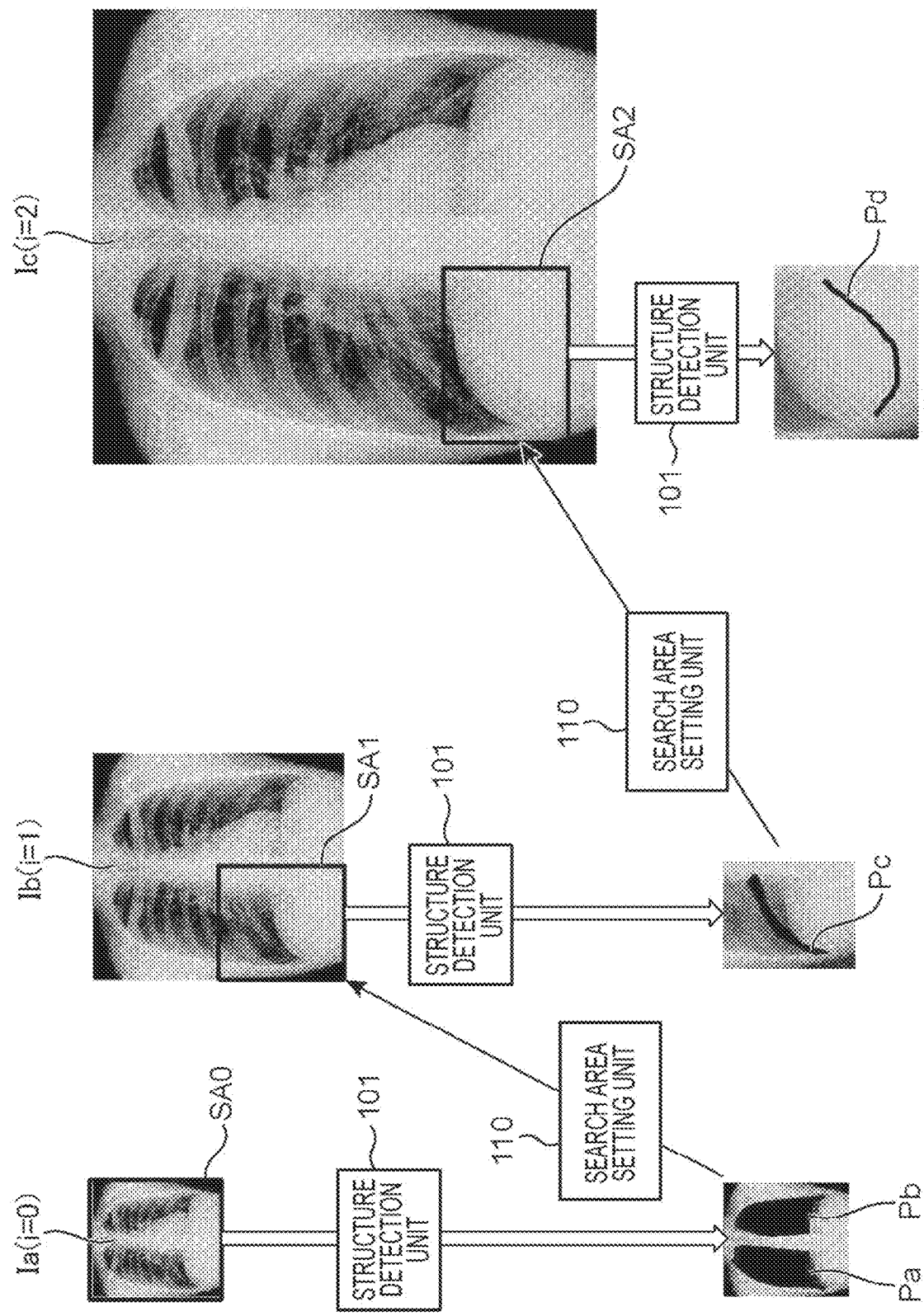
FIG. 27 is a diagram schematically illustrating steps illustrated in FIG. 25.

FIG. 27 is a diagram schematically illustrating steps S103 to S106 illustrated in FIG. 25. In FIG. 27, first, the structure detection unit 101 detects structures Pa and Pb from a chest X-ray image Ia whose resolution is low (i=0) (step S103). In the example illustrated in FIG. 27, the structure Pa is the right lung field, and the structure Pb is the left lung field. In the present embodiment, the chest X-ray image Ia is an example of a first X-ray image, the resolution i=0 (256×256) is an example of a first resolution, and the size of the structures Pa and Pb is an example of the first size.

Next, the resolution i is incremented (step S104), and the search area setting unit 110 sets a search area in a chest X-ray image Ib whose resolution is intermediate (i=1) (step S106). Although FIG. 27 illustrates only a search area SA1, a search area is set in step S106 for each of the structure IDs associated with the resolution i. Each search area is set using a structure to be detected indicated by a structure ID and a positional relationship between already detected structures (the structures Pa and Pb in the example illustrated in FIG. 27) saved in the normal model storage unit 103.

Next, the structure detection unit 101 detects a structure in the search area of the chest X-ray image Ib of the intermediate resolution (i=1) (step S103). Although FIG. 27 illustrates only a structure Pc detected in the search area SA1, a structure to be detected is detected in step S103 in each search area. In the present embodiment, the chest X-ray image Ib is an example of a second X-ray image, the resolution i=1 (512×512) is an example of a second resolution, and the size of the structure Pc is an example of the second size.

Next, the resolution i is incremented (step S104), and the search area setting unit 110 sets a search area in a chest X-ray image Ic whose resolution is high (i=2) (step S106). Although FIG. 27 illustrates only a search area SA2, a search area is set in step S106 for each of the structure IDs associated with the resolution i. Each search area is set using a structure to be detected indicated by a structure ID and a positional relationship between already detected structures (the structures Pa and Pb in the example illustrated in FIG. 27) saved in the normal model storage unit 103.

Next, the structure detection unit 101 detects a structure in the search area of the chest X-ray image Ic of the high resolution (i=2) (step S103). Although FIG. 27 illustrates only a structure Pd detected in the search area SA2, a structure to be detected is detected in step S103 in each search area.

As described above, according to the second embodiment of the present disclosure, when a deep neural network such as U-Net is used as the structure detection unit 101, a decrease in structure detection performance can be suppressed since a search area smaller than a target chest X-ray image is set when a high-resolution image is used even if the memory capacity of the GPU is low.

Third Embodiment

Figure 28:
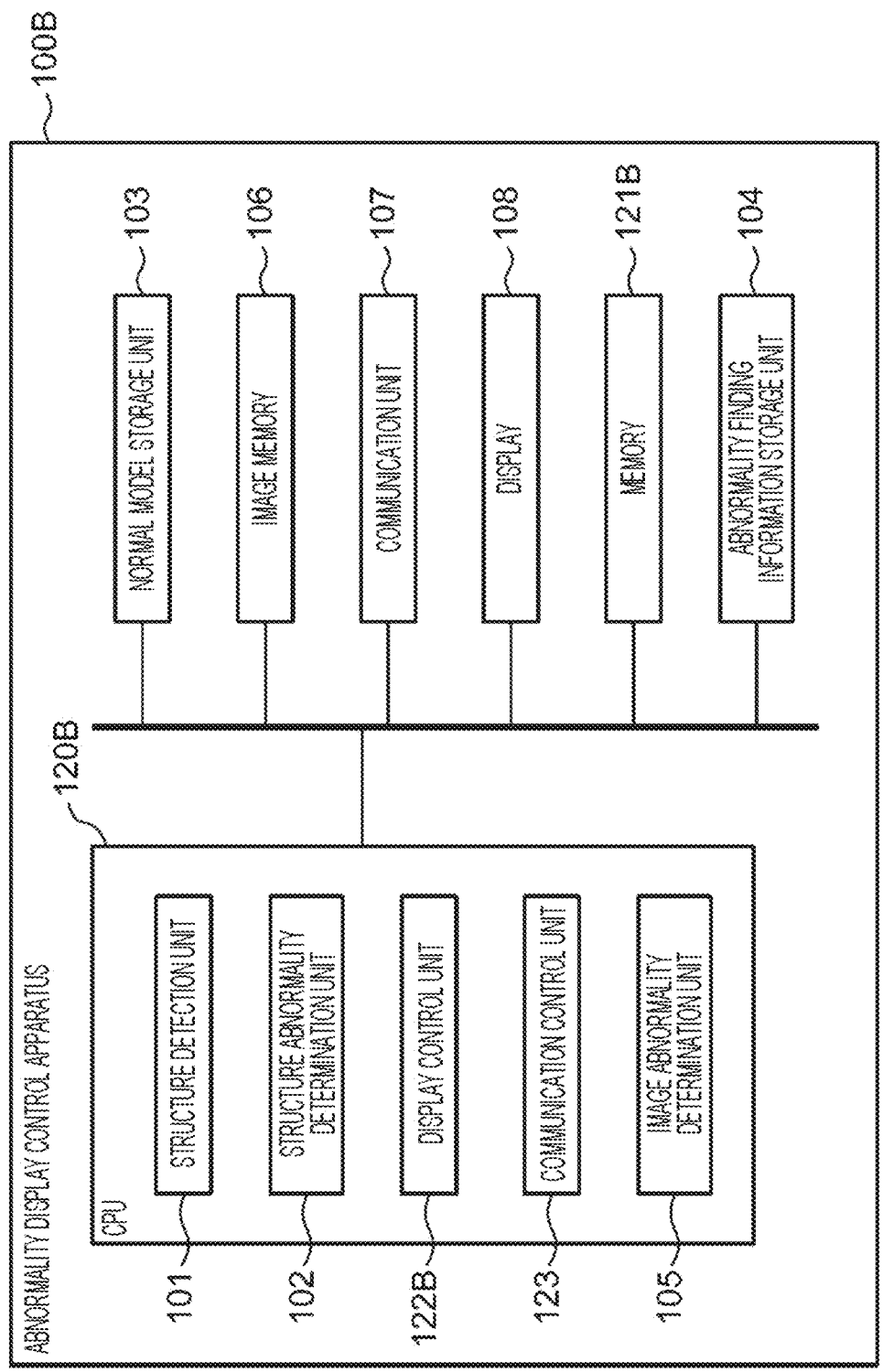
FIG. 28 is a block diagram illustrating the configuration of an abnormality display control apparatus according to a third embodiment.

FIG. 28 is a block diagram schematically illustrating the configuration of an abnormality display control apparatus 100B that performs a method for controlling display of an abnormality in a chest X-ray image according to a third embodiment. Unlike the abnormality display control apparatus 100 illustrated in FIG. 1, the abnormality display control apparatus 100B illustrated in FIG. 28 newly includes an abnormal finding information storage unit 104 and also includes a CPU 120B instead of the CPU 120 and a memory 121B instead of the memory 121.

The abnormal finding information storage unit 104 (an example of an abnormal finding memory) is achieved, for example, by a hard disk or a semiconductor memory. An example of information stored in the abnormal finding information storage unit 104 will be described later. The memory 121B is configured in the same manner as the memory 121 and includes, for example, a ROM, a RAM, and an EEPROM. The ROM of the memory 121B stores a control program for operating the CPU 120B according to the third embodiment.

The CPU 120B executes the control program according to the third embodiment stored in the memory 121B to function as the structure detection unit 101, the structure abnormality determination unit 102, a display control unit 122B, the communication control unit 123, and an image abnormality determination unit 105. The image abnormality determination unit 105 determines abnormal findings regarding the entirety of a target chest X-ray image on the basis of results of processing performed by the structure detection unit 101 and the structure abnormality determination unit 102 and information stored in the normal model storage unit 103 and the abnormal finding information storage unit 104. In addition to achieving the functions of the display control unit 122, the display control unit 122B also displays, on the display 108, the abnormal findings determined by the image abnormality determination unit 105 and suspected names of diseases.

Figure 29:
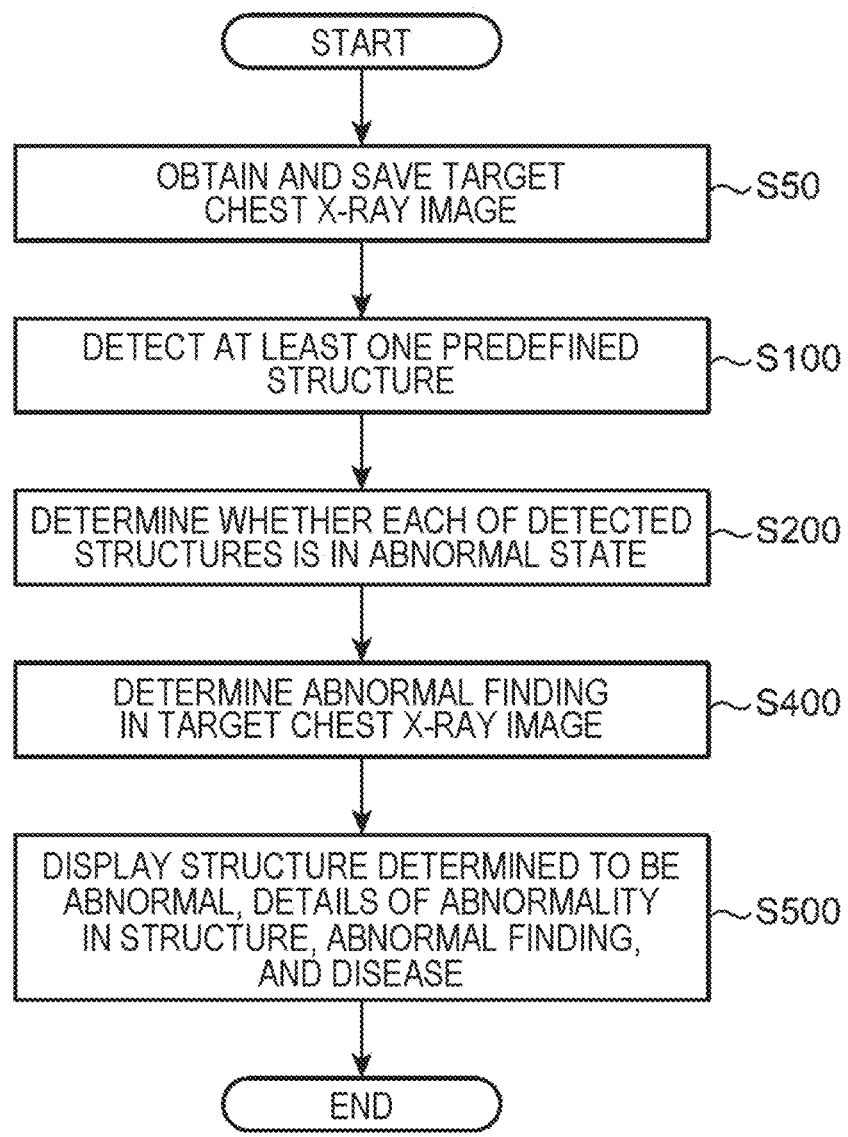
FIG. 29 is a flowchart according to the third embodiment.

FIG. 29 is a flowchart schematically illustrating a process performed by the abnormality display control apparatus 100B according to the third embodiment. Steps S50, S100, and S200 illustrated in FIG. 29 are the same as those illustrated in FIG. 3. In step S400, which follows step S200, the image abnormality determination unit 105 determines an abnormal finding in a target chest X-ray image on the basis of abnormal states of one or more structures and abnormal finding information 3000 (FIG. 30) stored in the abnormal finding information storage unit 104.

FIG. 30 is a diagram schematically illustrating the abnormal finding information 3000 stored in the abnormal finding information storage unit 104. As illustrated in FIG. 30, the abnormal finding information 3000 includes a structure ID field 3001, an indicator field 3002, an abnormal finding field 3003, and a disease field 3004. In the structure ID field 3001, structure IDs determined to be in an abnormal state are described. In the indicator field 3002, indicators corresponding to structure IDs determined to be in an abnormal state are described. In the abnormal finding field 3003, findings when corresponding structure IDs are determined to be in an abnormal state with corresponding indicators are described. In the disease field 3004, suspected diseases based on corresponding findings described in the abnormal finding field 3003 are described.

If the structure abnormality determination unit 102 determines that an angle between structures 1 and 8 is abnormal, for example, the image abnormality determination unit 105 determines that an abnormal finding is "X2" and that a suspected disease is "Y3" on the basis of the abnormal finding information 3000 stored in the abnormal finding information storage unit 104.

In step S500 illustrated in FIG. 29, the display control unit 122B displays, on the display 108, a target chest X-ray image, a structure determined by the structure abnormality determination unit 102 to be in an abnormal state, details of the abnormality, and an abnormal finding and a name of a suspected disease determined by the image abnormality determination unit 105. After step S500 ends, the process illustrated in FIG. 29 ends.

Figure 31:
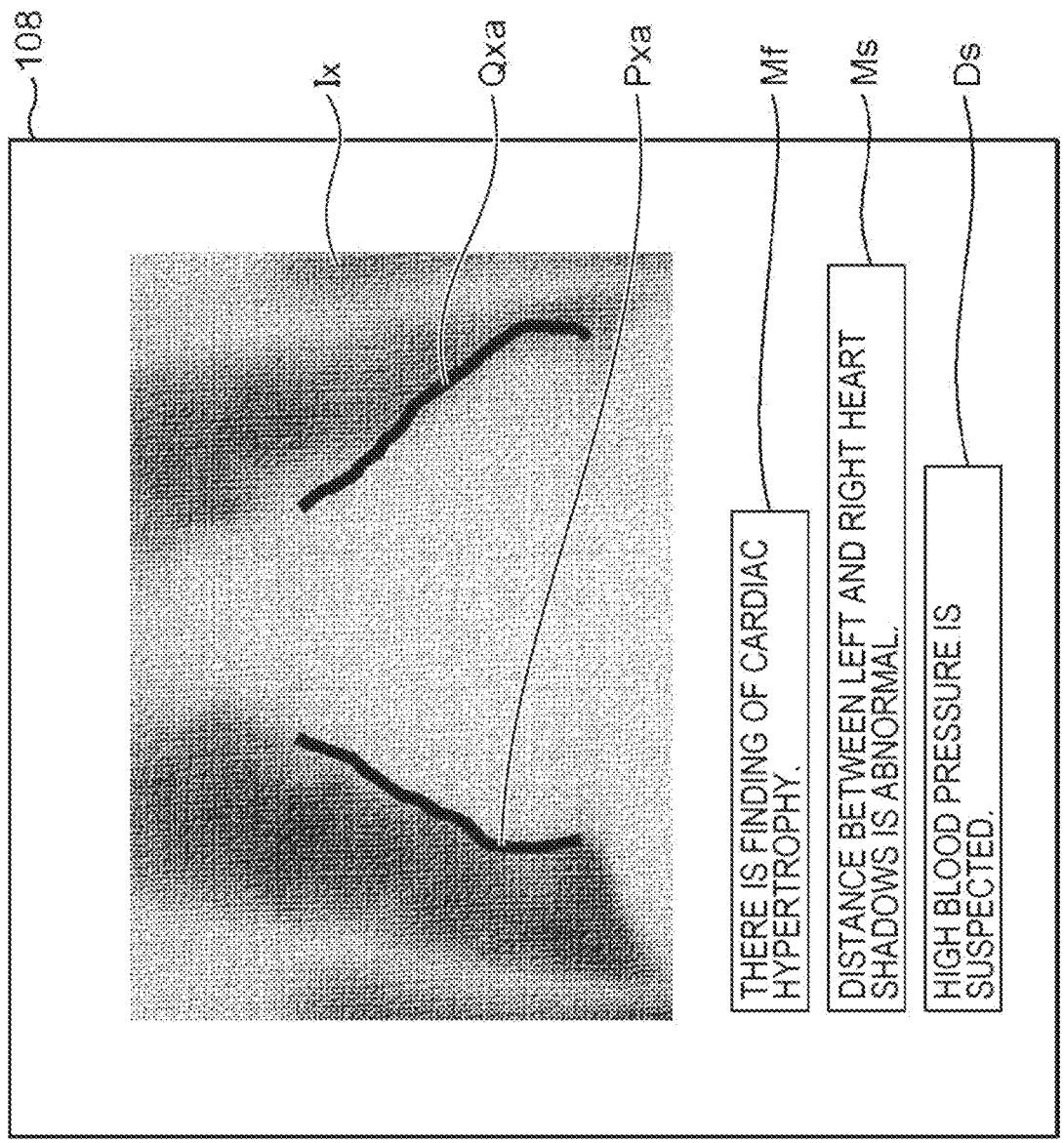
FIG. 31 is a diagram illustrating an example of a screen of a display according to the third embodiment.

FIG. 31 is a diagram schematically illustrating an example of a screen of the display 108. As illustrated in FIG. 31, the display control unit 122B displays, on the display 108, the target chest X-ray image Ix, the structures Pxa and Qxa determined to be in an abnormal state, a determined abnormal finding Mf, a message Ms indicating details of the abnormality in the structures Pxa and Pxa, which is a reason for the abnormal finding Mf, and a name Ds of a suspected disease. In FIG. 31, for example, the structures Pxa and Qxa determined to be in an abnormal state are a right heart shadow and a left heart shadow, respectively, and a reason for the abnormality is a distance. The display 108, therefore, displays "cardiac hypertrophy" as the abnormal finding Mf and "high blood pressure" as the name Ds of the suspected disease.

As described above, according to the third embodiment of the present disclosure, an abnormal finding in a chest X-ray image, a position of a structure that is a reason for the abnormal finding, details of the abnormality in the structure, and a name of a suspected disease are presented to the user. Not only a position of a detected lesion and/or a name of a disease but also information beneficial to the user, namely how a certain structure is different from a normal state, can thus be presented to the user. As a result, not only an interpretation doctor but also a clinician or a radiologist can give a diagnosis or study by himself/herself, or a medical student can be educated or study by himself/herself.

Fourth Embodiment

Figure 32:
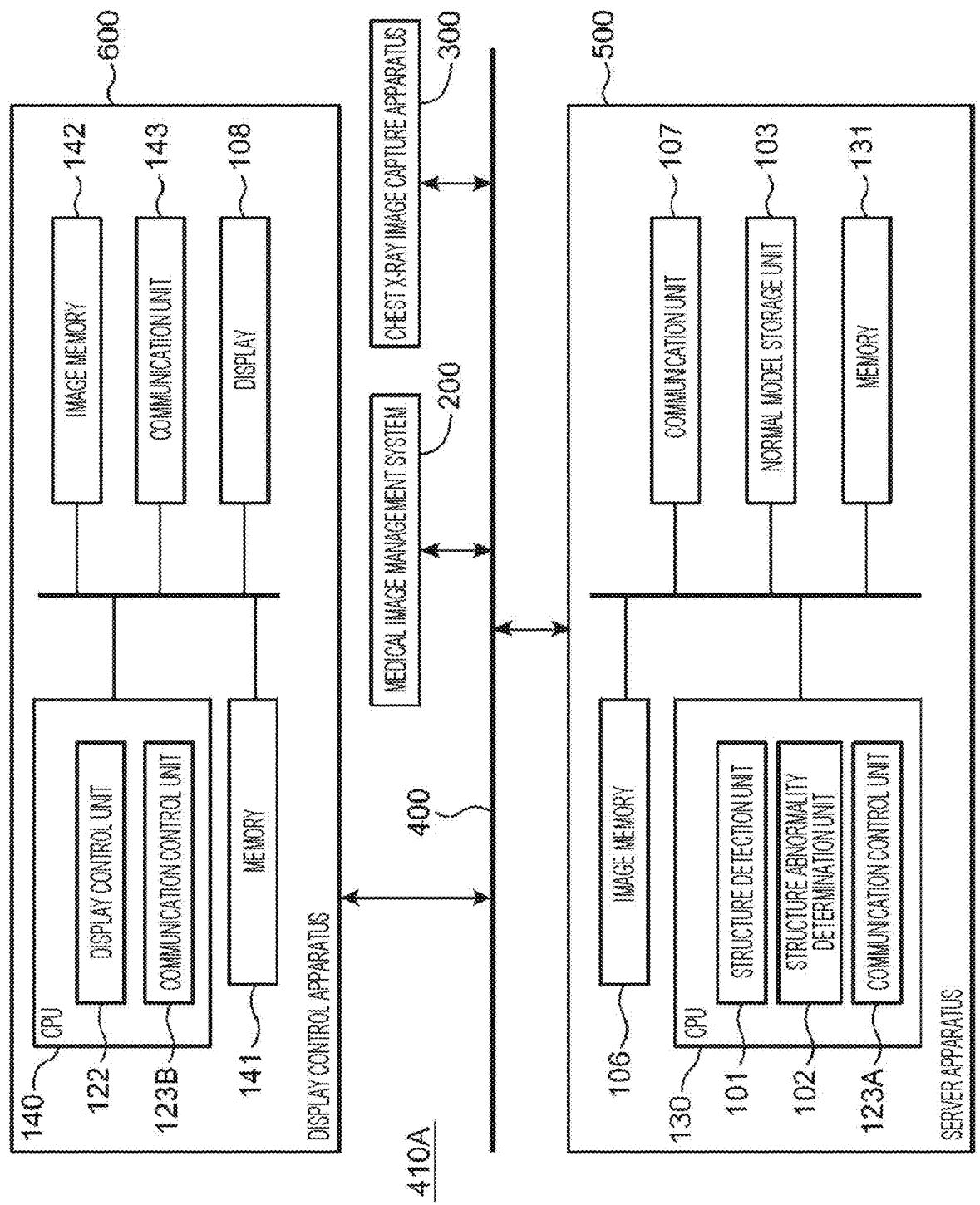
FIG. 32 is a block diagram illustrating a network configuration in a medical facility according to a fourth embodiment.

FIG. 32 is a block diagram schematically illustrating a network configuration 410A in a medical facility according to a fourth embodiment. As illustrated in FIG. 32, a server apparatus 500, a display control apparatus 600, the medical image management system 200, and the chest X-ray image capture apparatus 300 are connected to an intra network 400 in the medical facility in the fourth embodiment.

The server apparatus 500, the display control apparatus 600, the medical image management system 200, and the chest X-ray image capture apparatus 300 need not necessarily be connected to the intra network 400 in a single medical facility. The display control apparatus 600 and the medical image management system 200 may be software that operates on a server in a data center outside the medical facility, a private cloud server, a public cloud server, or the like, instead.

As illustrated in FIG. 32, the server apparatus 500 includes the normal model storage unit 103, the image memory 106, the communication unit 107, a CPU 130, and a memory 131. The memory 131 is achieved, for example, by a semiconductor memory. The memory 131 includes, for example, a ROM, a RAM, and an EEPROM. The ROM of the memory 131 stores a control program for operating the CPU 130.

The CPU 130 executes the control program stored in the memory 131 to function as the structure detection unit 101 (an example of a detection unit), the structure abnormality determination unit 102 (an example of a determination unit), and a communication control unit 123A (an example of an obtaining unit). The communication control unit 123A obtains a target chest X-ray image from the medical image management system 200 through the communication unit 107 and saves the obtained target chest X-ray image to the image memory 106. The communication control unit 123A transmits a result of detection performed by the structure detection unit 101 and a result of a determination made by the structure abnormality determination unit 102 to the display control apparatus 600 through the communication unit 107.

The display control apparatus 600 (an example of a terminal apparatus) is achieved, for example, by a tablet computer and carried by a medical worker such as a doctor or a radiologist. As illustrated in FIG. 32, the display control apparatus 600 includes a CPU 140, a memory 141, an image memory 142, a communication unit 143, and the display 108.

The memory 141 is achieved, for example, by a semiconductor memory. The memory 141 includes, for example, a ROM, a RAM, and an EEPROM. The ROM of the memory 141 stores a control program for operating the CPU 140. The CPU 140 executes the control program stored in the memory 141 to function as the display control unit 122 and a communication control unit 123B.

The communication control unit 123B receives, through the communication unit 143, data regarding a target chest X-ray image transmitted from the server apparatus 500 and stores the received data in the image memory 142. The communication control unit 123B also receives, through the communication unit 143, data regarding structures Pxa and Qxa determined to be in an abnormal state and a message Ms indicating details of the abnormality in the structures Pxa and Qxa transmitted from the server apparatus 500 and stores the received data in the memory 141. The display control unit 122 displays the same screen as in FIG. 23 on the display 108 on the basis of the information transmitted from the server apparatus 500.

According to the fourth embodiment, the same effect as that produced by the first embodiment can be produced. Alternatively, the CPU 130 of the server apparatus 500 may function as the structure detection unit 101, the structure abnormality determination unit 102, the communication control unit 123, the resolution conversion unit 109 (FIG. 24), and the search area setting unit 110 (FIG. 24). In this case, the same effect as that produced by the second embodiment can be produced. Alternatively, the CPU 130 of the server apparatus 500 may function as the structure detection unit 101, the structure abnormality determination unit 102, the communication control unit 123, and the image abnormality determination unit 105 (FIG. 28), and the CPU 140 of the display control apparatus 600 may function as the display control unit 122B (FIG. 28). In this case, the same effect as that produced by the third embodiment can be produced.

The present disclosure can be used in diagnosis aiding systems for chest X-ray images to be interpreted and interpretation education systems for medical students or interns.

What is claimed is:

1. A method for controlling display of an abnormality in a target chest X-ray image using a computer, the method comprising:
    obtaining the target chest X-ray image;
    detecting, in the target chest X-ray image using a model obtained as a result of machine learning, a structure including a linear structure formed of a first linear area drawn by projecting anatomical structures whose X-ray transmittances are different from each other or a second linear area drawn by projecting an anatomical structure including a wall of a trachea, a wall of a bronchus, or a hair line;
    calculating an indicator for determining an abnormal state from the structure, comparing the indicator with a reference indicator obtained in advance, and determining, on a basis of a result of the comparison, whether the structure is in the abnormal state; and
    displaying, if it is determined that the structure is in the abnormal state, an image of an area of the target chest X-ray image including the structure determined to be in the abnormal state and details of the abnormal state of the structure on a display.

2. The method according to claim 1,
    wherein the model obtained as a result of the machine learning is a model subjected to the machine learning such that the structure is detected in a learning chest X-ray image, which is a chest X-ray image in a normal state, using a neural network that performs prediction in units of pixels.

3. The method according to claim 2,
    wherein, in the detecting, a first X-ray image is created by converting a resolution of the target chest X-ray image into a first resolution, which is lower than the resolution of the target chest X-ray image,
    wherein a second X-ray image is created by converting the resolution of the target chest X-ray image into a second resolution, which is higher than the first resolution but equal to or lower than the resolution of the target chest X-ray image,
    wherein a structure of a first size is detected from the first X-ray image, wherein a search area smaller than the second X-ray image is set in the second X-ray image on a basis of a result of the detection of the structure of the first size, and wherein a structure of a second size, which is smaller than the first size, is detected in the search area.

4. The method according to claim 3, wherein, in the detection of the structure of the first size, an anatomical structure is detected from the first X-ray image as the structure of the first size, and wherein, in the detection of the structure of the second size, a linear structure is detected in the search area of the second X-ray image as the structure of the second size.

5. The method according to claim 3, wherein, in the setting of the search area, the search area is set using a relative positional relationship between the structure of the first size and the structure of the second size read from a position memory storing the relative positional relationship in advance.

6. The method according to claim 1, wherein, in the determining, a position of the linear structure is calculated as the indicator.

7. The method according to claim 6, wherein, in the determining, whether the structure is in the abnormal state is determined on a basis of a difference between the reference indicator read from a reference memory storing, as the reference indicator, an indicator calculated from structures detected from chest X-ray images in a normal state and the indicator calculated from the target chest X-ray image.

8. The method according to claim 1, wherein, in the determining, an angle between two linear structures is calculated as the indicator.

9. The method according to claim 1, wherein, in the determining, a distance between the two linear structures is calculated as the indicator.

10. The method according to claim 1, wherein, in the determining, area of the linear structure is calculated as the indicator.

11. The method according to claim 1, wherein, in the determining, width of the linear structure is calculated as the indicator.

12. The method according to claim 1, wherein, in the determining, an image pattern in an area sandwiched by two or more linear structures is calculated as the indicator.

13. The method according to claim 1, wherein, in the determining, an image pattern in a neighboring area of the linear structure is calculated as the indicator.

14. The method according to claim 1, further comprising:

reading a correspondence between an abnormal state of one or more structures and an abnormal finding in a chest X-ray image from an abnormal finding memory storing the correspondence and determining an abnormal finding in the target chest X-ray image from the determined abnormal state of the structure using the correspondence; and displaying the determined abnormal finding in the target chest X-ray image on the display.

15. A non-transitory computer-readable storage medium storing a program for causing a computer to perform a process, the process comprising:

obtaining a target chest X-ray image;

detecting, in the target chest X-ray image using a model obtained as a result of machine learning, a structure including a linear structure formed of a first linear area drawn by projecting anatomical structures whose X-ray transmittances are different from each other or a second linear area drawn by projecting an anatomical structure including a wall of a trachea, a wall of a bronchus, or a hair line;

calculating an indicator for determining a abnormal state from the structure, comparing the indicator with a reference indicator obtained in advance, and determining, on a basis of a result of the comparison, whether the structure is in the abnormal state; and displaying, if it is determined that the structure is in the abnormal state, an image of an area of the target chest X-ray image including the structure determined to be in the abnormal state and details of the abnormal state of the structure on a display.

16. An abnormality display control apparatus comprising:

a display;

an obtainer that obtains a target chest X-ray image, which is a chest X-ray image to be interpreted;

a detector that detects, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;

a determiner that calculates an indicator for determining the abnormal state from the structure, that compares the indicator with a reference indicator obtained in advance, and that determines, on a basis of a result of the comparison, whether the structure is in the abnormal state; and a display controller that displays, if it is determined that the structure is in the abnormal state, an image of an area of the target chest X-ray image including the structure determined to be in the abnormal state and details of the abnormal state of the structure on the display.

17. A server apparatus comprising:

an obtainer that obtains a target chest X-ray image, which is a chest X-ray image to be interpreted;

a detector that detects, in the target chest X-ray image using a model obtained as a result of machine learning, a structure including a linear structure formed of a first linear area that has been drawn by projecting anatomical structures whose X-ray transmittances are different from each other or a second linear area drawn by projecting an anatomical structure including a wall of a trachea, a wall of a bronchus, or a hair line;

a determiner that calculates an indicator for determining the abnormal state from the structure, that compares the indicator with a reference indicator obtained in advance, and that determines, on a basis of a result of the comparison, whether the structure is in the abnormal state; and a communication controller that transmits, if it is determined that the structure is in the abnormal state, an image of an area of the target chest X-ray image including the structure determined to be in the abnormal state and details of the abnormal state of the structure to an external terminal apparatus.

* * * * *